(12) United States Patent
Peet et al.

(10) Patent No.: US 8,188,146 B2
(45) Date of Patent: *May 29, 2012

(54) HIGHLY PURIFIED ETHYL EPA AND OTHER EPA DERIVATIVES

(75) Inventors: Malcolm Peet, Sheffield (GB); Krishna S. Vaddadi, Melbourne (AU)

(73) Assignee: Amarin Corporation Plc., Dublin (IE)

( * ) Notice: Subject to any disclaimer, the term of this patent is extended or adjusted under 35 U.S.C. 154(b) by 498 days.

This patent is subject to a terminal disclaimer.

(21) Appl. No.: 12/052,598

(22) Filed: Mar. 20, 2008

(65) Prior Publication Data

US 2008/0200547 A1    Aug. 21, 2008

Related U.S. Application Data

(60) Continuation of application No. 11/361,069, filed on Feb. 24, 2006, now abandoned, which is a continuation of application No. 10/014,603, filed on Dec. 14, 2001, now Pat. No. 6,689,812, which is a division of application No. 09/492,741, filed on Jan. 27, 2000, now Pat. No. 6,384,077.

(30) Foreign Application Priority Data

Jan. 27, 1999 (GB) .................................. 9901809.5

(51) Int. Cl.
*A01N 37/00* (2006.01)
*A61K 31/20* (2006.01)

(52) U.S. Cl. ...................................................... 514/560

(58) Field of Classification Search .................. None
See application file for complete search history.

(56) References Cited

U.S. PATENT DOCUMENTS

| | | | |
|---|---|---|---|
| 4,377,526 A | 3/1983 | Fujita et al. | |
| 4,526,902 A | 7/1985 | Rubin | |
| 4,935,243 A * | 6/1990 | Borkan et al. | 424/441 |
| 5,013,443 A | 5/1991 | Higashidate et al. | |
| 5,116,871 A | 5/1992 | Horrobin et al. | |
| 5,178,873 A | 1/1993 | Horrobin et al. | |
| 5,198,468 A | 3/1993 | Horrobin | |
| 5,215,630 A | 6/1993 | Hata et al. | |
| 5,252,333 A | 10/1993 | Horrobin | |
| 5,457,130 A | 10/1995 | Tisdale et al. | |
| 5,589,508 A | 12/1996 | Schlotzer et al. | |
| 5,603,959 A | 2/1997 | Horrobin et al. | |
| 5,618,558 A | 4/1997 | Horrobin et al. | |
| 5,760,081 A | 6/1998 | Leaf et al. | |
| 5,837,731 A | 11/1998 | Vaddadi | |
| 5,840,944 A | 11/1998 | Furihata et al. | |
| 5,888,541 A | 3/1999 | Horrobin et al. | |
| 6,069,168 A | 5/2000 | Horrobin et al. | |
| 6,331,568 B1 | 12/2001 | Horrobin | |
| 6,384,077 B1 | 5/2002 | Peet | |
| 6,531,150 B1 | 3/2003 | Sunohara et al. | |
| 6,555,700 B1 | 4/2003 | Horrobin et al. | |
| 6,689,812 B2 | 2/2004 | Peet | |
| 7,119,118 B2 | 10/2006 | Peet | |
| 2002/0077361 A1 | 6/2002 | Peet | |
| 2002/0183389 A1 | 12/2002 | Peet | |
| 2002/0193439 A1 | 12/2002 | Peet | |
| 2002/0198177 A1 | 12/2002 | Horrobin et al. | |
| 2003/0068216 A1 | 4/2003 | Takaiti | |
| 2003/0100610 A1 | 5/2003 | Shibuya et al. | |
| 2004/0077723 A1 | 4/2004 | Granata | |
| 2004/0078166 A1 | 4/2004 | Shin | |
| 2004/0162348 A1 | 8/2004 | Peet | |
| 2006/0142390 A1 | 6/2006 | Manku et al. | |
| 2006/0217356 A1 | 9/2006 | Wright et al. | |
| 2006/0252833 A1 | 11/2006 | Peet | |
| 2007/0017240 A1 | 1/2007 | Shapiro | |
| 2008/0200547 A1 | 8/2008 | Peet | |

FOREIGN PATENT DOCUMENTS

| | | |
|---|---|---|
| EP | 0 302 482 A2 | 2/1989 |
| EP | 0 460 917 A | 12/1991 |
| EP | 0 606 012 A | 7/1994 |
| EP | 0 610 506 A | 8/1994 |
| EP | 1 157 692 A1 | 11/2001 |
| EP | 1 296 670 B1 | 4/2003 |
| EP | 1 157 692 B1 | 10/2005 |
| GB | 2 148 713 A | 6/1985 |
| GB | 2 229 363 A | 9/1990 |
| GB | 9 901 809.5 | 1/1999 |
| JP | 04 182426 A | 6/1992 |
| WO | 90/04391 | 5/1990 |
| WO | 92/21335 | 12/1992 |
| WO | 94/28891 | 12/1994 |
| WO | 97/39759 A | 10/1997 |
| WO | 98/16216 | 4/1998 |
| WO | 99/29316 A | 6/1999 |
| WO | 01/15552 A1 | 3/2001 |
| WO | 02/02105 A1 | 1/2002 |

(Continued)

OTHER PUBLICATIONS

Aarsland, et al., "On the Effect of Peroximsomal β-Oxidation and Carnitine Palmitoyltransferase Activity by Eicosapentaenoic Aid in Live and Heart of Rats." Lipids, 25:546-548, (1990).

(Continued)

*Primary Examiner* — Leslie A. Royds Draper
(74) *Attorney, Agent, or Firm* — K&L Gates LLP

(57) ABSTRACT

A pharmaceutical preparation comprising EPA in an appropriately assimilable form where of all the fatty acids present in the preparation at least 90%, and preferably at least 95%, is in the form of EPA and where less than 5%, and preferably less than 3%, is in the form of DHA is provided.

10 Claims, 3 Drawing Sheets

FOREIGN PATENT DOCUMENTS

Figure 1:
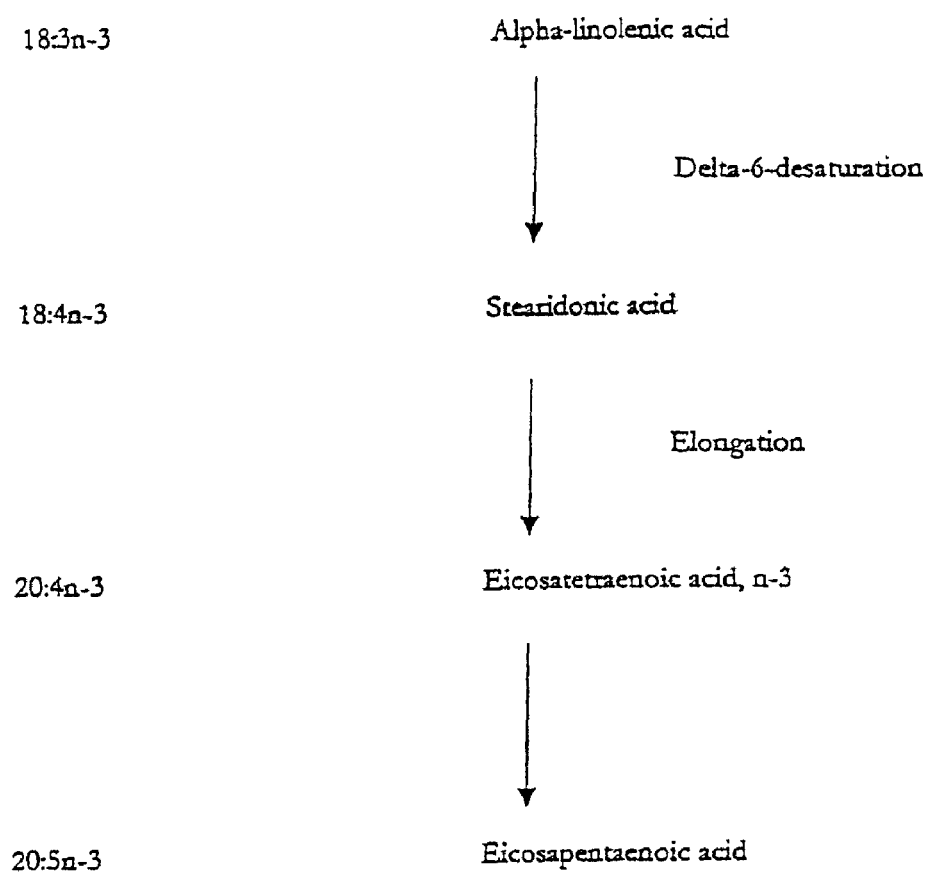

| WO | 02/058793 | A1 | 8/2002 |
|---|---|---|---|
| WO | 02/089787 | A1 | 11/2002 |
| WO | 02/096408 | | 12/2002 |
| WO | 03/068216 | | 8/2003 |
| WO | 2004/078166 | | 9/2004 |
| WO | 2007/017240 | | 2/2007 |

OTHER PUBLICATIONS

Aas, V, et al., "Eicosapentaenoic acid (20:5 n-3) increases fatty acid and glucose uptake in cultured human skeletal muscle cells." Journal of Lipid Research, 47:366-374 (2006).

Abbey, M, et al., "Effect of fish oil on lipoproteins, lecithin:cholesterol acyltransferase, and lipidtransfer protein activity in humans" Arterioscler. Thromb. Vasc. Biol. 10:85-94 (1990).

Adan, Y, et al., "Effects of docosahexaenoic and eicosapentaenoic acid on lipid metabolism, eicosanoid production, platelet aggregation and atherosclerosis." Biosci. Biotechnol. Biochem. 63(1), 111-119 (1999).

Adan, Y., et al., "Concentration of serum lipids and aortic lesion size in female and male apo E-deficient mice fed docosahexaenoic acid." Biosci. Biotechnol. Biochem. 63(2):309-313 (1999).

Agren, J.J., et al., "Fatty acid composition of erythrocyte, platelet, and serum lipids in strict vegans." Lipids 30:365-369 (1995).

Ait-Said, et al., "Inhibition by eicosapentaenoic acid of IL-1β-induced PGHS-2 expression in human microvascular endothelial cells: involvement of lipoxygenase-derived metabolites and p38 MAPK pathway." Biohimicia et Biophysica Acta, 1631:66-85 (2003).

Alessandri, J-M., et al., "Estradiol favors the formation of eicosapentaenoic acid (20:5n-3) and n-3 docosapentaenoic acid (22:5n-3) from alpha-linolenic acid (18:3n-3) in SH-SY5Y neuroblastoma cells." Lipids 43:19-28 (2008).

Allred, C., et al., "PPARγ1 as a molecular target of eicosapentaenoic acid in human colon cancer (HT-29) cells." J. Nutr. 138:250-256 (2008).

Ando, M, et al., "Eicosapentanoic acid reduces plasma levels of remnant lipoproteins and prevents in vivo peroxidation of LDL in dialysis patients." J. Am. Soc. Nephrol., 10:2177-2184( (1999).

Ando, Y., et al., "Positional distribution of highly unsaturated fatty acids in triacyl-sn-glycerols of Artemia Nauplii enriched with docosahexaenoic acid ethyl ester." Lipids 36:733-740 (2001).

Arshad, A., et al., "Sudden cardiac death and the role of medical therapy." Progress in Cardiovascular Diseases, vol. 50, No. 6, 420-438, (2008).

Arterbum, L., et al., "Distribution, interconversion, and dose response of n-3 fatty acids in humans." Am J Clin Nutr., 83:1467S-1476S (2006).

Asano, M., et al., "Inhibitory effects of ω-3 polyunsaturated fatty acids on receptor-mediated non-selective cation currents in rat A7r5 vascular smooth muscle cells." British Journal of Pharmacology 120:1367-1375, (1997).

Asano, M., et al., "Eicosapentaenoic acid inhibits vasopressin-activated Ca2q influx and cell proliferation in rat aortic smooth muscle cell lines." European Journal of Pharmacology 379:199-209 (1999).

Ayton, et al., "A pilot open case series of Ethyl-EPA supplementation in the treatment of anorexia nervosa," Prostaglandins, Leukotrienes and Essential Fatty Acids 71 (2004) pp. 205-209.

Ayton, et al., "Rapid improvement of severe anorexia nervosa during treatment with ethyl-eicosapentaenoate and micronutrients," European Psychiatry 19 (2004) pp. 317-319.

Banga, A., et al., "Adiponectin translation is increased by the PPARγ agonists pioglitazone and ω-3 fatty acids." Am J Physiol Endocrinol Metab 296:480-489 (2009).

Basu, A., et al., "Dietary Factors That Promote or Retard Inflammation." Arterioscler. Thromb. Vasc. Biol. 26:995-1001 (2006).

Belmaker, et al., "Addition of Omega-3 Fatty Acid to Maintenance Medication Treatment for Recurrent Unipolar Depressive Disorder," Am J Psychiatry 2002; 159:477-479.

Belmaker, et al., "Omega-3 Eicosapentaenoic Acid in Bipolar Depression: Report of a Small Open-Label Study," J Clin Psychiatry 2005 66:726-729.

Bénistant, C., et al., "Docosapentaenoic acid (22:5, n-3): metabolism and effect on prostacyclin production in endothelial cells." Prostaglandins, Leukotrienes and Essential Fatty Acids, 55(4):287-292, (1996).

Betteridge, D.J., "Diabetic dyslipidaemia: past, present and future." Practical Diabetes Int, 21(2): 78-85. (2004).

Block, R. C., et al., "EPA and DHA in blood cell membranes from acute coronary syndrome patients and controls." Atherosclerosis, 197(2):821-828 (2007).

Bousserouel, S., et al., "Different effects of n-6 and n-3 polyunsaturated fatty acids on the activation of rat smooth muscle cells by interleukin-1β." J. Lipid Res. 44:601-611 (2003).

Bousserouel, S. et al., "Modulation of cyclin D1 and early growth response factor-1 gene expression in interleukin-1β-treated rat smooth muscle cells by n-6 and n-3 polyunsaturated fatty acids." Eur. J. Biochem. 271:4462-4473 (2004).

Brady, L., et al., Increased n-6 polyunsaturated fatty acids do not attenuate the effects of long-chain n-3 polyunsaturated fatty acids on insulin sensitivity or triacylglycerol reduction in Indian Asians. Am J Clin Nutr 79:983-91(2004).

Breslow, J., "n-3 Fatty acids and cardiovascular disease." Am J Clin Nutr., 83:1477S-82S (2006).

Brossard, N., et al., "Retroconversion and metabolism of [13C]22:6n-3 in humans and rats after intake of a single dose of [13C]22:6n-3—3-triacyylglycerols." Am. J. Clin. Nutr. 64:577-86 (1996).

Brouwer, I.A., et al., "Effect of fish oil on ventricular tachyarrhythmia and death in patients with implantable cardioverter defibrillators." JAMA. 295(22):2613-2619 (2006).

Brown, A. J., et al., "Persistent changes in the fatty acid composition of erythrocyte membranes after moderate intake of n-3 polyunsaturated fatty acids: study design and implications." Am.J. Clin. Nutri. 54:668-73(1991).

Brown, A. J., et al., "Administration of n-3 Fatty Acids in the Diets of Rats or Directly to Hepatocyte Cultures Results in Different Effects on Hepatocellular ApoB Metabolism and Secretion." Arterioscler. Thromb. Vasc. Biol. 19:106-114 (1999).

Bryhn, M., et al., "The bioavailability and pharmacodynamics of different concentrations of omega-3 acid ethyl esters." Prostaglandins, Leukotrienes and Essential Fatty Acids 75:19-24 (2006).

Burdge, G.C., et al., "The effect of altering the 20:5n-3 and 22:6n-3 content of a meal on the postprandial incorporation of n-3 polyunsaturated fatty acids into plasma triacylglycerol and non-esterified fatty acids in humans." Prostaglandins, Leukotrienes and Essential Fatty Acids 77:59-65 (2007).

Burdge, G.C., et al., "Lack of effect of meal fatty acid composition on postprandial lipid, glucose and insulin responses in men and women aged 50-65 years consuming their habitual diets." British Journal of Nutrition, 96:489-500 (2006).

Burdge, G.C., et al., "Eicosapentaenoic and docosapentaenoic acids are the principal products of a-linolenic acid metabolism in young men." British Journal of Nutrition 88:355-363 (2002).

Burr, M. L., et al., "Effects of changes in fat, fish and fibre intakes on death and myocardial reinfarction: Diet and reinfarction trial." The Lancet, Sep. 30, 1989; 2(8666):757-61.

Calibresi, L., et al., "Omacor in familial combined hyperlipidemia: effects on lipids and low density lipoprotein subclasses." Atherosclerosis 148:387-396 (2000).

Cao, J., et al., "Incorporation and Clearance of Omega-3 Fatty Acids in Erythrocyte Membranes and Plasma Phospholipids." Clinical Chemistry 52(12):2265-2272 (2006).

Carroll, D. N., et al., "Evidence for the Cardioprotective Effects of Omega-3 Fatty Acids." Ann Pharmacother., 36:1950-6 (2002).

Cazzola, R., et al., "Age- and dose-dependent effects of an eicosapentaenoic acid-rich oil on cardiovascular risk factors in healthy male subjects." Atherosclerosis 193:159-167 (2007).

Chan, D.C., et al., "Randomized controlled trial of the effect of n-3 fatty acid supplementation on the metabolism of apolipoprotein B-100 and chylomicron remnants in men with visceral obesity." Am J Clin Nutr 77:300-7 (2003).

Chen, H. et al., "Eicosapentanoic acid inhibits hypoxia-reoxygenation-induced injury by attenuating upregulation of MMP-1 in adult rat myocytes." Cardiovascular Research 59:7-13 (2003).

Chen, H., et al., "EPA and DHA attenuate ox-LDL-induced expression of adhesion molecules in human coronary artery endothelial cells via protein kinase B pathway." Journal of Molecular and Cellular Cardiology 35:769-775 (2003).

Chen, I.S., et al., "In vitro clearance of chylomicron triglycerides containing (ω-3) eicosapentaenoate." Atherosclerosis, 65:193-198 (1987).

Christensen, J. H., et al, "Effect of fish oil on heart rate variability in survivors of myocardial infarction: a double blind randomised controlled trial." BMJ, 312:677-678 (1996).

Christensen, M.S., et al., "Intestinal absorption and lymphatic transport of eicosapentaenoic (EPA), docosahexaenoic (DHA), and decanoic acids: dependence on intramolecular triacyiglycerol structure." Am J Clin Nutr 61:56-61 (1995).

Cleland, L.G., et al., "A Biomarker of n-3 compliance in patients taking fish oil for rheumatoid arthritis." Lipids 38:419-424 (2003).

Colhoun, H. M. et al, "Primary prevention of cardiovascular disease with atorvastatin in type 2 diabetes in the Collaborative Atorvastatin Diabetes Study (CARDS): multicentre randomised placebo-controlled trial." Lancet 364: 685-9 (2004).

Collins, N., et al., "Differences between Dietary Supplement and Prescription Drug Omega-3 Fatty Acid Formulations: A Legislative and Regulatory Perspective." Journal of the American College of Nutrition, 27 (6):659-666 (2008).

Conklin, S. M., et al., "Serum ω-3 fatty acids are associated with variation in mood, personality and behavior in hypercholesterolemic community volunteers." Psychiatry Research 152: 1-10 (2007).

Contacos, C., et al., "Effect of pravastatin and ω-3 fatty acids on plasma lipids and lipoproteins in patients with combined hyperlipidemia." Arterioscler. Thromb. Vasc. Biol. 13:1755-1762 (1993).

Crowe, F. L., et al., "Serum phospholipid n☐3 long-chain polyunsaturated fatty acids and physical and mental health in a population-based survey of New Zealand adolescents and adults." Am J Clin Nutr 86:1278-85 (2007).

Daggy, B., et al., Dietary fish oil decreases VLDL production rates. Biochimica et Biophysics Acta 920: 293-300 (1987).

Das, U.N., Essential fatty acids as possible mediators of the actions of statins. Prostaglandins, Leukotrienes and Essential FattyAcids 65(1):37-40, (2001).

De Caterina, R., et al., "The Omega-3 fatty acid docosahexaenoate reduces cytokine-induced expression of proatherogenic and proinflammatory proteins in human endothelial cells." Arterioscler. Thromb. Vasc. Biol. 14:1829-1836 (1994).

De Caterina, R, et al., "Control of Endothelial Leukocyte Adhesion Molecules by Fatty Acids." Lipids, vol. 31:S57-S63 (1996).

Deckelbaum, R. J., et al., "Conclusions and recommendations from the symposium, Beyond Cholesterol: Prevention and Treatment of Coronary Heart Disease with n-3 Fatty Acids." Am J Clin Nutr 87:2010S-12S (2008).

Dewailly, E., et al., "n-3 Fatty acids and cardiovascular disease risk factors among the Inuit of Nunavik." Am J Clin Nutr 74:464-73 (2001).

Dijk, J. M., et al., "Carotid intima—media thickness and the risk of new vascular events in patients with manifest atherosclerotic disease: the SMART study." European Heart Journal 27:1971-1978 (2006).

Dodin, S., et al., "Flaxseed on cardiovascular disease markers in healthy menopausal women: a randomized, double-blind, placebo-controlled trial." Nutrition 24:23-30 (2008).

Dullenmeijer, C., et al., "n-3 Fatty acid proportions in plasma and cognitive performance in older adults." Am J Clin Nutr 86:1479-85 (2007).

Duncan, R. E., et al., "Regulation of HMG-CoA reductase in MCF-7 cells by genistein, EPA, and DHA, alone and in combination with mevastatin." Cancer Letters 224:221-228 (2005).

Dwyer, J. H., et al., "Arachidonate 5-Lipoxygenase Promoter Genotype, Dietary Arachidonic Acid, and Atherosclerosis." N. Engl. J. Med., 350:1 (2004).

Dyerberg, J. et al., "Marine Oils and Thrombogenesis." Prog. Lipid Res. 21:255-269 (1982).

El-Sohemy, A., et. al. "Regulation of Mevalonate Synthesis in Low Density Lipoprotein Receptor Knockout Mice Fed n-3 or n-6 Polyunsaturated Fatty Acids." Lipids, 34 (10): 1037-43 (1999).

Engler, M.B., et al., "Mechanisms of vasorelaxation induced by eicosapentaenoic acid (20:5n-3) in WKY rat aorta." British Journal of Pharmacology 131:1793-1799 (2000).

Engler, M.M., et al. "The effects of a diet rich in docosahexaenoic acid on organ and vascular fatty acid composition in spontaneously hypertensive rats." Prostaglandins, Leukotrienes and Essential Fatty Acids 61(5):289-295 (1999).

Faggin, E., et al., "Fish Oil Supplementation Prevents Neointima Formation in Nonhypercholesterolemic Balloon-Injured Rabbit Carotid Artery by Reducing Medial and Adventitial Cell Activation." Arterioscler. Thromb. Vasc. Biol., 20:152-163 (2000).

Fer, M., et al., "Metabolism of eicosapentaenoic and docosahexaenoic acids by recombinant human cytochromes P450." Archives of Biochemistry and Biophysics 471:116-125 (2008).

Ferns, G., et al., "Investigation and management of hypertriglyceridaemia." J. Clin. Pathol. 61:1174-1183 (2008).

Fischer, R., et al., "Dietary n-3 polyunsaturated fatty acids and direct renin inhibition improve electrical remodeling in a model of high human renin hypertension." Hypertension 51:540-546 (2008).

Flaten, H., et al., "Fish-oil concentrate: effects on variables related to cardiovascular disease." Am. J. Clin. Nutr. 52:300-306 (1990).

Ford, E.S. et al., "Hypertriglyceridemia and Its Pharmacologic Treatment Among US Adults." Arch. Intern. Med., 169(6): 572-78 (2009).

Friedman, A. N., et al., "Fish Consumption and Omega-3 Fatty Acid Status and Determinants in Long-Term Hemodialysis." Amer. J. Kidney Diseases, 47(6):1064-1071 (2006).

Frøyland, L., et al., "Hypotriacylglycerolemic component of fish oil." Prostaglandins, Leukotrienes and Essential Fatty Acids 57:387-388 (1997).

Goto, Y., et al., "Clinical Pharmacological Trial of Ethyl Icosapentate (MND-21)—Dose Finding Study." Journal of Clinical Therapeutic & Medicines 8:1293-309 (1992).

Griffin, M.D., et al., "Effects of altering the ratio of dietary n-6 to n-3 fatty acids on insulin sensitivity, lipoprotein size, and postprandial lipemia in men and postmenopausal women aged 45-70 y: the OPTILIP Study." Am J Clin Nutr 84:1290-8 (2006).

Guallar, E., et al., "Omega-3 fatty acids in adipose tissue and risk of myocardial infarction—The EURAMIC study." Arterioscler. Thromb. Vasc. Biol., 19:1111-1118 (1999).

Guizy, M., et al. "ω-3 and ω-6 Polyunsaturated fatty acids block HERG channels." Am J Physiol Cell Physiol 289:C1251-C1260 (2005).

Harkonarson, H., et al., "Effects of a 5-lipoxygenase-activating protein inhibitor on biomarkers associated with risk of myocardial infarction—a randomized trial." JAMA, 293(8):2245-56 (2005).

Hall, W. L., et al., "A high-fat meal enriched with eicosapentaenoic acid reduces postprandial arterial stiffness measured by digital volume pulse analysis in healthy men." J. Nutr. 138: 287-291 (2008).

Han, J. J., et al., "Enhancement of both reaction yield and rate of synthesis of structured triacylglycerol containing eicosapentaenoic acid under vacuum with water activity control." Lipids 34:989-995 (1999).

Hanasaki, K., et al., "Potent modification of low density lipoprotein by group X secretory phospholipase A2 is linked to macrophage foam cell formation." J. Biol. Chem. 277(32):29116-24 (2002).

Hansen, J-B, et al., "Effects of highly purified eicosapentaenoic acid and docosahexaenoic acid on fatty acid absorption, incorporation into serum phospholipids and postprandial triglyeridemia." Lipids 33:131-38 (1998).

Harris, W. S., et al., "Influence of n-3 fatty acid supplementation on the endogenous activities of plasma lipases." Am. J. Clin. Nutr. 66:254-60 (1997).

Harris, W. S., et al., "n-3 Fatty acids and urinary excretion of nitric oxide metabolites in humans." Am. J. Clin. Nutr., 65:459-64 (1997).

Harris, W.S., et al., "Omega-3 fatty acids and coronary heart disease risk: Clinical and mechanistic perspectives." Atherosclerosis 197:12-24 (2008).

Harris, W.S., "n-3 Fatty acids and serum lipoproteins: human studies." Am J Clin Nutr 65:1645S-54S (1997).

Harris, W.S., "n-3 Fatty acids and human lipoprotein metabolism: an update." Lipids 34:S257-S258 (1999).

Harris, W. S., "The omega-3 index as a risk factor for coronary heart disease." Am J Clin Nutr 87:1997S-2002S (2008).

Harris, W.S., et al., "Stearidonic acid increases the red blood cell and heart eicosapentaenoic acid content in dogs." Lipids 42:325-333 (2007).

Harris, W. S., et al., "Tissue n-3 and n-6 fatty acids and risk for coronary heart disease events." Atherosclerosis 193:1-10 (2007).

Harris, W.S.., "Expert opinion: omega-3 fatty acids and bleeding—cause for concern?" The American Journal of Cardiology 99(6A): 45C-46C (2007).

Harris, W. S., "Fish oils and plasma lipid and lipoprotein metabolism in humans: a critical review." J Lipid Res. 30:785-807 (1989).

Harris, W.S., "Omega-3 fatty acids in cardiac biopsies from heart transplantation patients." Circulation 110;1645-1649 (2004).

Harris, W.S., et al., "Comparison of the effects of fish and fish-oil capsules on the n-3 fatty acid content of blood cells and plasma phospholipids." Am J Clin Nutr 86:1621-5 (2007).

Hibbeln, J. R., et al., "Healthy intakes of n-3 and n-6 fatty acids: estimations considering worldwide diversity." Am J Clin Nutr. 83:1483S-93S (2006).

Hilpert, K.F., et al., "Postprandial effect of n-3 polyunsaturated fatty acids on apolipoprotein B-containing lipoproteins and vascular reactivity in type 2 diabetes." Am J Clin Nutr 85:369-76 (2007).

Hirafuji, M., et al., "Docosahexaenoic acid potentiates interleukin-lb induction of nitric oxide synthase through mechanism involving p44/42 MAPK activation in rat vascular smooth muscle cells." British Journal of Pharmacology 136:613-619 (2002).

Holmeide, A. K., et al., "Oxidative degradation of eicosapentaenoic acid into polyunsaturated aldehydes." Tetrahedron 59:7157-7162 (2003).

Hombeck, M., et al., "Biosynthesis of the algal pheromone fucoserratene by the freshwater diatom *Asterionella formosa* (Bacillariophyceae)." Tetrahedron 54:11033-11042 (1998).

Howe, P.R.C., et al., "Equal antithrombotic and triglyceride-lowering effectiveness of eicosapentaenoic acid-rich and docosahexaenoic acid-rich fish oil supplements." Lipids 34:S307-S308 (1999).

Inoue, I., et al., "Expression of peroxisome proliferator-activated receptor α(PPARα) in primary cultures of human vascular endothelial cells." Biochem. Biophys. Res. Comm., 246, 370-374 (1998).

Ishida, Y., et al., "α-Lipoic Acid and Insulin Autoimmune Syndrome." Diabeters Care, 30(9): 2240-41 (2007).

Jacobson, T.A., "Role of n-3 fatty acids in the treatment of hypertriglyceridemia and cardiovascular disease." Am J Clin Nutr 87:1981S-90S (2008).

Jialal, I., "Editorial: Remnant lipoproteins: measurement and clinical significance." Clinical Chemistry 48(2):217-219 (2002).

Jung, U.J., et al., "n-3 Fatty acids and cardiovascular disease: mechanisms underlying beneficial effects." Am J Clin Nutr 87: 2003S-9S (2008).

Kanayasu, T., et al., "Eicosapentaenoic acid inhibits tube formation of vascular endothelial cells in vitro." Lipids 26:271-276 (1991).

Katan, M. B., et al., "Kinetics of the incorporation of dietary fatty acids into serum cholesteryl esters, erythrocyte membranes, and adipose tissue: an 18-month controlled study." J. Lipid Res. 38: 2012-2022 (1997).

Kato, T., et al., "Palmitate impairs and eicosapentaenoate restores insulin secretion through regulation of SREBP-1c in pancreatic islets." Diabetes, 57(9):2382-2392 (2008) (published online May 5, 2008.).

Kawashima, H., et al., "Oral Administration of Dihomo-γ-Linolenic Acid Prevents Development of Atopic Dermatitis in NC/Nga Mice." Lipids 43:37-43 (2008).

Kelley, D. S., et al., "Docosahexaenoic Acid Supplementation Decreases Remnant-Like Particle-Cholesterol and Increases the (n-3) Index in Hypertriglyceridemic Men." J. Nutr. 138: 30-35 (2008).

Kew, S., et al., "Effects of oils rich in eicosapentaenoic and docosahexaenoic acids on immune cell composition and function in healthy humans." Am J Clin Nutr 79:674-81 (2004).

Kimura, F., et al., "Long-term supplementation of docosahexaenoic acid-rich, eicosapentaenoic acid-free microalgal oil in n-3 fatty acid-deficient rat pups." Biosci. Biotechnol. Biochem., 72(2):608-610 (2008).

Kinsella, J.E., et al., "Dietary n-3 polyunsaturated fatty acids and amelioration of cardiovascular disease: possible mechanisms." Am J Clin Nutr 52:1-28 (1990).

Kohno, M., et al., "Inhibition by Eicosapentaenoic Acid of Oxidized-LDL- and Lysophosphatidylcholine-Induced Human Coronary Artery Smooth Muscle Cell Production of Endothelin." J. Vasc. Res. 38:379-388 (2001).

Kojima, T,. et al., "Long-term administration of highly purified eicosapentaenoic acid provides improvement of psoriasis." Dermatologica, 182:225-230 (1991).

Kosonen, O., et al., "Inhibition by nitric oxide-releasing compounds of E-selectin expression in and neutrophil adhesion to human endothelial cells." European Journal of Pharmacology 394:149-156 (2000).

Kris-Ehterton, P. M., et al., "Omega-3 Fatty Acids and Cardiovascular Disease—New Recommendations From the American Heart Association." Arterioscler Thromb Vasc Biol. 23:151-152 (2003).

Ku, K., et al., "Beneficial Effects of ω-3 Fatty Acid Treatment on the Recovery of Cardiac Function After Cold Storage of Hyperlipidemic Rats." Metabolism, 48(10):123-1209 (1999).

Kurabayashi, T., et al., "Eicosapentaenoic acid effect on hyperlipidemia in menopausal japanese women." Obstet Gynecol 96:521-8 (2000).

Laidlaw, M, et al., "Effects of supplementation with fish oil—derived n-3 fatty acids and γ-linolenic acid on circulating plasma lipids and fatty acid profiles in women." Am J Clin Nutr 77:37-42 (2003).

Larsen, L.N., et al., "Heneicosapentaenoate (21:5n-3): Its incorporation into lipids and its effects on arachidonic acid and eicosanoid Synthesis." Lipids 32:707-714 (1997).

Leaf, A., "Historical overview of n−3 fatty acids and coronary heart disease." Am J Clin Nutr 87:1978S-80S. (2008).

Lee, J.H., et al., "Omega-3 fatty acids for cardioprotection." Mayo Clin Proc., 83(3):324-332 (2008).

Lemaitre, R.N., et al., "n-3 Polyunsaturated fatty acids, fatal ischemic heart disease, and nonfatal myocardial infarction in older adults: the Cardiovascular Health Study." Am J Clin Nutr 77:319-25 (2003).

Li, H., et al., "EPA and DHA reduce LPS-induced inflammation responses in HK-2 cells: Evidence for a PPAR-γ-dependent mechanism." Kidney Intl. 67:867-74 (2005).

Li, D., et al., "Effect of dietary a-linolenic acid on thrombotic risk factors in vegetarian men." Am J Clin Nutr 69:872-82 (1999).

Lin, Y., et al., "Differential effects of eicosapentaenoic acid on glycerolipid and apolipoprotein B metabolism in primary human hepatocytes compared to HepG2 cells and primary rat hepatocytes." Biochimica et Biophysica Acta 1256:88-96 (1995).

Lohmussaar, E., et al., "ALOX5AP Gene and the PDE4D Gene in a Central European Population of Stroke Patients." Stroke, 36:731-736 (2005).

Lucas, M., et al., "Ethyl-eicosapentaenoic acid for the treatment of psychological distress and depressive symptoms in middle-aged women: a double-blind, placebo-controlled, randomized clinical trial." Am J Clin Nutr 89:641-51 (2009).

Madsen, L., et al., "Eicosapentaenoic and Docosahexaenoic Acid Affect Mitochondrial and Peroxisomal Fatty Acid Oxidation in Relation to Substrate Preference." Lipids 34:951-963 (1999).

Mallat, Z., et al., "Protective role of interleukin-10 in atherosclerosis." Circ. Res. 85:e17-e24 (1999).

Mallat, Z., et al., "Apoptosis in the vasculature: mechanisms and functional importance." British Journal of Pharmacology 130:947-962 (2000).

Marckmann, P., "Fishing for heart protection." Am J Clin Nutr, 78:1-2 (2003).

Mater, M.K., et al., "Arachidonic acid inhibits lipogenic gene expression in 3T3-L1 adipocytes through a prostanoid pathway." J. Lipid Res. 39:1327-1334 (1998).

Matsumoto, M., et al., "Orally administered eicosapentaenoic acid reduces and stabilizes atherosclerotic lesions in ApoE-deficient mice." Atherosclerosis, 197(2):524-533 (2008).

McMurchie, E.J., et al., "Incorporation and effects of dietary eicosapentaenoate (20 : 5( n-3)) on plasma and erythrocyte lipids of the marmoset following dietary supplementation with differing levels of linoleic acid." Biochimica et Biophysics Acta, 1045:164-173 (1990).

Merched, A.J., et al., "Atherosclerosis: evidence for impairment of resolution of vascular inflammation governed by specific lipid mediators." FASEB J. 22:3595-3606 (2008).

Metcalf, R.G., et al., "Effects of fish-oil supplementation on myocardial fatty acids in humans." Am J Clin Nutr 85:1222-28 (2007).

Metcalf, R.G. et al., "Effect of dietary n-3 polyunsaturated fatty acids on the inducibility of ventricular tachycardia in patients with ischemic cardiomyopathy." Am J Cardiol 101:758-761 (2008).

Mii, S., et al., "Perioperative use of eicosapentaenoic acid and patency of infrainguinal vein bypass: a retrospective chart review." Curr Ther Res Clin Exp. 68:161-174 (2007).

Miller, M., et al., "Impact of lowering triglycerides on raising HDL-C in hypertriglyceridemic and non-hypertriglyceridemic subjects." International Journal of Cardiology 119:192-195 (2007).

Minihane, A.M., et al., "ApoE polymorphism and fish oil supplementation in subjects with an atherogenic lipoprotein phenotype." Arterioscler. Thromb. Vasc. Biol. 20:1990-1997 (2000).

Mishra, A., et al., "Oxidized omega-3 fatty acids inhibit NF-κB activation via a PPARα-Dependent Pathway." Arterioscler Thromb Vasc Biol. 24:1621-1627 (2004).

Mizuguchi, K., et al., "Mechanism of the lipid-lowering effect of ethyl all-cis-5,8,11,14,17-icosapentaenoate." European Journal of Pharmacology, 231:121-127 (1993).

Mizuguchi, K., et al., "Ethyl all-cis-5,8,11,14,17-icosapentaenoate modifies the biochemical properties of rat very low-density lipoprotein." European Journal of Pharmacology, 231:221-227 (1993).

Morita, I., et al., "Effects of purified eicosapentaenoic acid on arachidonic acid metabolism in cultured murine aortic smooth muscle cells, vessel walls and platelets." Lipids 18:42-490 (1983).

Mostad, I.L, et al., "Effects of n-3 fatty acids in subjects with type 2 diabetes: reduction of insulin sensitivity and time-dependent alteration from carbohydrate to fat oxidation." Am J Clin Nutr 84:540-50 (2006).

Mozaffarian, D., "Fish and n-3 fatty acids for the prevention of fatal coronary heart disease and sudden cardiac death." Am J Clin Nutr, 87:1991S-6S (2008).

Mozaffarian, D., et al., "Dietary fish and ω-3 fatty acid consumption and heart rate variability in US adults." Circulation, 117:1130-1137 (2008).

Naba, H., et al., "Improving effect of ethyl eicosapentanoate on statin-induced rhabdomyolysis in *Eisai hyperbilirubinemic* rats." Biochemical and Biophysical Research Communications, 340:215-220 (2006).

Nakamura, H., et al., "Evaluation of ethyl icosapentate in the treatment of hypercholesterolemia in kidney transplant recipients." Transplantation Proceedings, 30:3047-3048 (1998).

Nambi, V., et al., "Combination therapy with statins and omega-3 fatty acids." Am J Cardiol 98:34i-38i (2006).

Nattel, S., et al., "Atrial remodeling and atrial fibrillation: Mechanisms and implications." Circ Arrhythmia Electrophysiol, 1:62-73 (2008).

Negre-Salvayre, A., et al., "Advanced lipid peroxidation end products in oxidative damage to proteins. Potential role in diseases and therapeutic prospects for the inhibitors." British Journal of Pharmacology 153:6-20 (2008).

Nobukata, H., et al., "Long-term administration of highly purified eicosapentaenoic acid ethyl ester prevents diabetes and abnormalities of blood coagulation in male WBN/Kob rats." Metabolism, 49(12): 912-919 (2000).

Nobukata, H., et al., "Long-term administration of highly purified eicosapentaenoic acid ethyl ester improves the dysfunction of vascular endothelial and smooth muscle cells in male WBN/Kob rats." Metabolism, 49(12): 1588-1591 (2000).

Nobukata, H., et al., "Age-related changes in coagulation, fibrinolysis, and platelet aggregation in male WBN/Kob rats." Thrombosis Research 98: 507-516 (2000).

Nourooz-Zadeh, J., et al., "Urinary 8-epi-PGF2α and its endogenous β-oxidation products (2,3-dinor and 2,3-dinor-5,6-dihydro) as biomarkers of total body oxidative stress." Biochemical and Biophysical Research Communications 330:731-736 (2005).

O'Donnell, C.J., et al., "Leukocyte telomere length and carotid artery intimal medial thickness—the Framingham heart study." Arteriosclerosis, Thrombosis, and Vascular Biology.28:1165-1171 (2008).

Okuda, Y., et al., "Long-term effects of eicosapentaenoic acid on diabetic peripheral neuropathy and serum lipids in patients with type II diabetes mellitus." Journal of Diabetes and Its Complications 10:280-287 (1996).

Okumura, T., et al., "Eicosapentaenoic acid improves endothelial function in hypertriglyceridemic subjects despite increased lipid oxidizability." Am J Med Sci 324(5):247-253 (2002).

Oliw, E.H., et al., "Biosynthesis of prostaglandins from 17(18)epoxy-eicosatetraenoic acid, a cytochrome P-450 metabolite of eicosapentaenoic acid." Biochimica el Biophysica Acta, 1126 (1092) 261-268.

Park, Y., et al., "Omega-3 fatty acid supplementation accelerates chylomicron triglyceride clearance." J. Lipid Res. 44:455-463 (2003).

Pownall, H.J., et al., "Correlation of serum triglyceride and its reduction by ω-3 fatty acids with lipid transfer activity and the neutral lipid compositions of high-density and low-density lipoproteins." Atherosclerosis 143:285-297 (1999).

Puri, et al., "Eicosapentaenoic Acid in Treatment-Resistant Depression Associated with Symptom Remission, Structural Brain Changes and Reduced Neuronal Phospholipid Turnover," Int J Clinical Practice 2001; 55:560-563.

Qi, K., et al., "Omega-3 fatty acid containing diets decrease plasma triglyceride concentrations in mice by reducing endogenous triglyceride synthesis and enhancing the blood clearance of triglyceride-rich particles." Clinical Nutrition 27(8):424-430 (2008).

Raitt, M.H., et al., "Fish oil supplementation and risk of ventricular tachycardia and ventricular fibrillation in patients with implantable defibrillators—a randomized controlled trial." JAMA. 293(23):2884-2891 (2005).

Rambjor, G.S. et al., "Eicosapentaenoic acid is primarily responsible for hypotriglyeridemic effect of fish oil in humans." Lipids, 31:S45-S49 (1996).

Reiffel, J.A., et al., "Antiarrhythmic effects of omega-3 fatty acids." Am J Cardiol 98:50i-60i (2006).

Riediger, N.D., et al., "A systemic review of the roles of n-3 fatty acids in health and disease." J Am Diet Assoc. 109:668-679. (2009).

Risé, P., et al., "Effects of simvastatin on the metabolism of polyunsaturated fatty acids and on glycerolipid, cholesterol, and de novo lipid synthesis in THP-1 cells." J. Lipid Res. 38:1299-1307 (1997).

Roche, H.M., et al., "Effect of long-chain n-3 polyunsaturated fatty acids on fasting and postprandial triacylglycerol metabolism." Am J Clin Nutr 71:232S-7S (2000).

Roche, H.M., et al., "Long-chain n-3 polyunsaturated fatty acids and triacylglycerol metabolism in the postprandial state." Lipids 34: S259-S265 (1999).

Rustan, A.C., et al., "Eicosapentaenoic acid reduces hepatic synthesis and secretion of triacylglycerol by decreasing the activity of acyl-coenzyme A:1,2-diacylglycerol acyltransferase." J. Lipid Res. 29:1417-1426 (1988).

Rustan, A.C., et al., "Postprandial decrease in plasma unesterified fatty acids during n-3 fatty acid feeding is not caused by accumulation of fatty acids in adipose tissue." Biochimica et Biophysica Acta 1390.245-25 (1998).

Rustan, A.C., et al., "Eicosapentaenoic acid inhibits cholesterol esterification in cultured parenchymal cells and isolated microsomes from rat liver." J. Bio. Chem. 263(17):8126-32 (1988).

Ryan, A.M., et al., "Enteral nutrition enriched with eicosapentaenoic acid (EPA) preserves lean body mass following esophageal cancer surgery: results of a double-blinded randomized controlled trial." Ann Surg 249:355-363 (2009).

Saito, J., et al., "Mechanisms of enhanced production of PGI2 in cultured rat vascular smooth muscle cells enriched with eicosapentaenoic acid." Atherosclerosis 131: 219-228 (1997).

Sanders, T.A., et al., "Triglyceride-lowering effect of marine polyunsaturates in patients with hypertriglyceridemia." Arterioscler. Thromb. Vasc. Biol. 5:459-465 (1985).

Sanders, T.A., et al., "Effect of varying the ratio of n-6 to n-3 fatty acids by increasing the dietary intake of α-linolenic acid, eicosapentaenoic and docosahexaenoic acid, or both on fibrinogen and clotting factors VII and XII in persons aged 45-70 y: the OPTILIP Study." Am J Clin Nutr 84:513-22 (2006).

Sasaki, Y.F., et al., "Bio-anticlastogenic effects of unsaturated fatty acids included in fish oil—docosahexaenoic acid, docosapentaenoic acid, and eicosapentaenoic acid—in cultured Chinese hamster cells." Mutation Research, 320: 9-22 (1994).

Satoh, N., et al., "Purified eicosapentaenoic acid reduces small dense LDL, remnant lipoprotein particles, and C-reactive protein in metabolic syndrome." Diabetes Care, 30(1): 144-146 (2007).

Schectman, G., et al., "Heterogeneity of Low Density Lipoprotein Responses to Fish-Oil Supplementation in Hypertriglyceridemic Subjects." Arterioscler. Thromb. Vasc. Biol. 9:345-354 (1989).

Schmidt, E.B., et al., "Lipoprotein-associated phospholipase A2 concentrations in plasma are associated with the extent of coronary artery disease and correlate to adipose tissue levels of marine n-3 fatty acids." Atherosclerosis 196: 420-424 (2008).

Schmitz, G., et al., "The opposing effects of n-3 and n-6 fatty acids." Progress in Lipid Research, 47:147-155 (2008).

Schwarz, S., et al., "Lycopene inhibits disease progression in patients with benign prostate hyperplasia." J. Nutr. 138: 49-53 (2008).

Serhan, C.N., et al., "Resolvins: A family of bioactive products of omega-3 fatty acid transformation circuits initiated by aspirin treatment that counter proinflammation signals." J. Exp. Med. 196:1025-1037 (2002).

Shan, Z., et al., "A combination study of spin-trapping, LC/ESR and LC/MS on carbon-centred radicals formed from lipoxygenase-catalysed peroxidation of eicosapentaenoic acid." Free Radical Research, 43(1):13-27 (2009).

Shimizu, H., et al., "Long-term effect of eicosapentaenoic acid ethyl (EPA-E) on albuminuria of non-insulin dependent diabetic patients." Diabetes Research and Clinical Practice 28: 35-40 (1995).

Sierra, S., et al., "Dietary eicosapentaenoic acid and docosahexaenoic acid equally incorporate as decosahexaenoic acid but differ in inflammatory effects." Nutrition 24: 245-254 (2008).

Simoens, C.M., et al., "Inclusion of 10% fish oil in mixed medium-chain triacylglycerol—longchain triacylglycerol emulsions increases plasma triacylglycerol clearance and induces rapid eicosapentaenoic acid (20:5n-3) incorporation into blood cell phospholipids." Am J Clin Nutr 88: 282-8 (2008).

Singh, R.B., et al., "Randomized, double-blind, placebo-controlled trial of fish oil and mustard oil in patients with suspected acute myocardial infarction: the Indian experiment of infarct survival—4." Cardiovascular Drugs and Therapy 11:485-491 (1997).

Sohma, R. et al., "Protective effect of n-3 polyunsaturated fatty acid on primary culture of rat hepatocytes without glycemic alterations." Journal of Gastroenterology and Hepatology 22: 1965-1970 (2007).

Spector, A.A., et al. "Epoxyeicosatrienoic acids (EETs): metabolism and biochemical function." Progress in Lipid Research 43: 55-90 (2004).

Spector, A.A., "Arachidonic acid cytochrome P450 epoxygenase pathway." Journal of Lipid Research, 50: S52-S56 (2009) (published online on Oct. 23, 2008.).

Springer, T.A., "Traffic signals for lymphocyte recirculation and leukocyte emigration: The multistep paradigm." Cell, 76: 301-314 (1994).

Stalenhoef, A.F.H., et al., "The effect of concentrated n-3 fatty acids versus gemfibrozil on plasma lipoproteins, low density lipoprotein heterogeneity and oxidizability in patients with hypertrygliceridemia." Atherosclerosis 153: 129-138 (2000).

Stark, K.D., et al., "Effect of a fish-oil concentrate on serum lipids in postmenopausal women receiving and not receiving hormone replacement therapy in a placebo-controlled, double-blind trial." Am J Clin Nutr 72:389-94 (2000).

Stark, K.D, et al., "Differential eicosapentaenoic acid elevations and altered cardiovascular disease risk factor responses after supplementation with docosahexaenoic acid in postmenopausal women receiving and not receiving hormone replacement therapy." Am J Clin Nutr 79:765-73 (2004).

Stark, K.D., "The percentage of n-3 highly unsaturated fatty acids in total HUFA as a biomarker for omega-3 fatty acid status in tissues." Lipids 43:45-53 (2008).

Sugiyama, E., et al., "Eicosapentaenoic acid lowers plasma and liver cholesterol levels in the presence of peroxisome proliferators-activated receptor alpha." Life Sciences, 83:19-28 (2008).

Surette, M.E., et al., "Evidence for mechanisms of the hypotriglyceridemic effect of n-3 polyunsaturated fatty, acids." Biochimica et Biophysic Acta, 1126: 199-205 (1992).

Tanaka, K.T., et al. "Reduction in the recurrence of stroke by eicosapentaenoic acid for hypercholesterolemic patients—Subanalysis of the JELIS trial." Stroke, 39(7):2052-8 (2008).

Tedgui, A., et al., "Anti-inflammatory mechanisms in the vascular wall." Circ. Res. 88:877-887 (2001).

Theilla, M., et al., "A diet enriched in eicosapentanoic acid, gamma-linolenic acid and antioxidants in the prevention of new pressure ulcer formation in critically ill patients with acute lung injury: A randomized, prospective, controlled study." Clinical Nutrition 26: 752-757 (2007).

Thies, F., et al., "Dietary supplementation with eicosapentaenoic acid, but not with other long-chain n-3 or n-6 polyunsaturated fatty acids, decreases natural killer cell activity in healthy subjects aged >55 y." Am J Clin Nutr 73:539-48 (2001).

Thies, F., et al., "Association of n-3 polyunsaturated fatty acids with stability of atherosclerotic plaques: a randomised controlled trial." Lancet 361: 477-85 (2003).

Ullian, M.E., "Fatty acid inhibition of angiotensin II-stimulated inositol phosphates in smooth muscle cells." Am J Physiol Heart Circ Physiol 264: H595-H603 (1993).

Van der Steeg, W.A., et al., "High-density lipoprotein cholesterol, high-density lipoprotein particle size, and apolipoprotein A-I: Significance for cardiovascular risk—the IDEAL and EPIC-Norfolk studies." J. Am. Coll. Cardiol. 51;634-642 (2008).

Vedin, I., et al., "Effects of docosahexaenoic acid-rich n-3 fatty acid supplementation on cytokine release from blood mononuclear leukocytes: the OmegAD study." Am J Clin Nutr 87:1616-22 (2008).

Vidgren, H.M., et al., "Incorporation of n-3 fatty acids into plasma lipid fractions, and erythrocyte membranes and platelets during dietary supplementation with fish, fish oil, and docosahexaenoic acid-rich oil among healthy young men." Lipids 32: 697-705 (1997).

Volcik, K.A., et al., "Peroxisome proliferator-activated receptor αgenetic variation interacts with n-6 and long-chain n-3 fatty acid intake to affect total cholesterol and LDL-cholesterol concentrations in the Atherosclerosis Risk in Communities Study." Am J Clin Nutr 87:1926-31 (2008).

Von Schacky, C., "A review of omega-3 ethyl esters for cardiovascular prevention and treatment of increased blood triglyceride levels." Vascular Health and Risk Management 2(3): 251-262 (2006).

Wada, M., et al., "Enzymes and receptors of prostaglandin pathways with arachidonic acid-derived versus eicosapentaenoic acid-derived substrates and products." J. Biol. Chem. 282(31): 22254-22266 (2007).

Walldius, G., et al., "Editorial: Rationale for using apolipoprotein B and apolipoprotein A-I as indicators of cardiac risk and as targets for lipid-lowering therapy." European Heart Journal 26,210-212 (2005).

Wander, R.C., et al., "Influence of long.chain polyunsaturated fatty acids on oxidation of low density lipoprotein." Prostaglandins, Leukotrienes and Essential Fatty Acids 59(2):143-151 (1998).

Wang, L., et al., "Triglyceride-rich lipoprotein lipolysis releases neutral and oxidized FFAs that induce endothelial cell inflammation." J. Lipid Res. 50:204-213 (2009).

Wang, C., et al.. "n-3 Fatty acids from fish or fish-oil supplements, but not α-linolenic acid, benefit cardiovascular disease outcomes in primary- and secondary-prevention studies: a systematic review." Am J Clin Nutr 84:5-17 (2006).

Weaver, K.L., et al., "Effect of Dietary Fatty Acids on Inflammatory Gene Expression in Healthy Humans." J. Biol. Chem., 284(23): 15400-15407 (2009) (published online Apr. 9, 2009.).

Weber, P., "Triglyceride-lowering effect of n-3 long chain polyunsaturated fatty acid: eicosapentaenoic acid vs. docosahexaenoic acid." Lipids 34: S269 (1999).

Westphal, S., et al., "Postprandial chylomicrons and VLDLs in severe hypertriacylglycerolemia are lowered more effectively than are chylomicron remnants after treatment with n23 fatty acids." Am J Clin Nutr 71:914-920 (2000).

Whelan, J., et al., "Evidence that dietary arachidonic acid increases circulating triglycerides." Lipids 30, 425-429 (1995).

Wierzbicki, A.S., "Editorial: Newer, lower, better? Lipid drugs and cardiovascular disease—the continuing story." Int J Clin Pract, 61(7):1064-1067 (2007).

Wierzbicki, A.S., "Editorial: Raising HDL-C: back to the future?" Int J Clin Pract, 61(7): 1069-1071 (2007).

Willumsen, N., et al., "Eicosapentaenoic acid, but not docosahexaenoic acid, increased, mitochondrial fatty acid oxidation and upregulates 2,3-dienoyl-CoA reductase gene expression in rats." Lipids, 31:579-592 (1996).

Wojenski, C.M., et al., "Eicosapentaenoic acid ethyl ester as an antithrombotic agent: comparison to an extract of fish oil." Biochimica et Biophysica Acta. 1081:33-38 (1991).

Wong, S.H., et al., "Effects of eicosapentaenoic and docosahexaenoic acids on Apoprotein B mRNA and secretion of very low density lipoprotein in HepG2 cells." Arterioscler. Thromb. Vasc. Biol. 9;836-841 (1989).

Woodman, R.J., et al., "Effects of purified eicosapentaenoic and docosahexaenoic acids on glycemic control, blood pressure, and serum lipids in type 2 diabetic patients with treated hypertension." Am J Clin Nutr 76:1007-15 (2002).

Woodman, R.J., et al., "Effects of purified eicosapentaenoic acid and docosahexaenoic acid on platelet, fibrinolytic and vascular function in hypertensive type 2 diabetic patients." Atherosclerosis 166: 85-93 (2003).

Xiao, Y-F., et al. "Blocking effects of polyunsaturated fatty acids on $Na^+$ channels of neonatal rat ventricular myocytes." Proc. Natl. Acad. Sci. 92: 11000-11004 (1995).

Xiao, Y-F., et al. "Fatty acids suppress voltage-gated $Na^+$ currents in HEK293t cells transfected with the a-subunit of the human cardiac $Na^+$ channel." Proc. Natl. Acad. Sci. 95: 2680-2685 (1998).

Xiao, Y-F., et al. "Inhibitory effect of n-3 fish oil fatty acids on cardiac $Na^+/Ca^{2+}$ exchange currents in HEK293t cells." Biochemical and Biophysical Research Communications 321: 116-123 (2004).

Yamashita, N., et al., "Inhibition of natural killer cell activity of human lymphocytes by eicosapentaenoic acid." Biochem. Biophys. Res. Comm. 138(3): 1058-1067 (1986).

Yang, S.P., et al., "Eicosapentaenoic acid attenuates vascular endothelial growth factor-induced proliferation via inhibiting Flk-1 receptor expression in bovine carotid artery endothelial cells." J. Cell. Physio. 176:342-349 (1998).

Yano, T., et al., "Effects of ethyl-all-*cis*-5,8,11,14,17-icosapentaenoate (EPA-E), pravastatin and their combination on serum lipids and intimal thickening of cuff-sheathed carotid artery in rabbits." Life Sciences, 61(20):2007-2015 (1997).

Yerram, N.R., et al., "Eicosapentaenoic acid metabolism in brain microvessel endothelium: effect on postaglandin formation." J. Lipid Res.30:1747-1757 (1989).

Zaima, N., et al., "*Trans* geometric isomers of EPA decrease LXRa-induced cellular triacylglycerol via suppression of SREBP-1c and PGC-1β." J. Lipid Res. 47: 2712-2717 (2006).

Zanarini, et al., "Omega-3 Fatty Acid Treatment of Women with Borderline Personality Disorder: A Double-Blind, Placebo-Controlled Pilot Study," Am J Psychiatry 2003; 160:167-169.

Zhang, Y.W., et al., "Pretreatment with eicosapentaenoic acid prevented hypoxia/reoxygenation-induced abnormality in endothelial gap junctional intercellular communication through inhibiting the tyrosine kinase activity." Prostaglandins, Leukotrienes and Essential Fatty Acids 61(1): 33-40 (1999).

Zhang, Y.W., et al., "Inhibitory effects of eicosapentaenoic acid (EPA) on the hypoxia/reoxygenation-induced tyrosine kinase activation in cultured human umbilical vein endothelial cells." Prostaglandins, Leukotrienes and Essential FattyAcids 67(4):253-261 (2002).

Zhang, M., et al., "Effects of eicosapentaenoic acid on the early stage of type 2 diabetic nephropathy in KKAy/Ta mice: involvement of anti-inflammation and antioxidative stress." Metabolism Clinical and Experimental 55:1590-1598 (2006).

Zhao, G., et al., "Dietary α-linolenic acid reduces inflammatory and lipid cardiovascular risk factors in hypercholesterolemic men and women." J. Nutr. 134: 2991-2997 (2004).

Zhao, G. et al., "Dietary α-linolenic acid inhibits proinflammatory cytokine production by peripheral blood mononuclear cells in hypercholesterolemic subjects." Am J Clin Nutr 85:385-91 (2007).

Ziegler, D., et al., "Treatment of symptomatic diabetic polyneuropathy with the antioxidant αlipoic acid: A 7-month multicenter randomized controlled trial (ALADIN III Study)." Diabetes Care 22:1296-1301 (1999).

Zuijdgeest-van Leeuwen, S.D., et al. "Incorporation and washout of orally administered n-3 fatty acid ethyl esters in different plasma lipid fractions." British Journal of Nutrition 82:481-488 (1999).

Alderman, JD. et al. (1989). Effect of a modified, well-tolerated niacin regimen on serum total cholesterol, high density lipoprotein cholesterol and the cholesterol to high density lipoprotein ratio. Am. J. Cardiol. 64: 725-729.

Andrade, SE. et al. (1995). Discontinuation of antihyperlipidaemic drugs_do rates reported in clinical trials reflect rates in primary care settings? New Eng. J. Med. 332: 1125-1131.

Andrew L. Stoll et al, Arch. Gen. Psychiatry, vol. 56, "Omega 3 Fatty Acids in Bipolar Disorder", pp. 407-412, May 1999.

Appelton, Katherine M., et al. "Effects of n-3 long-chain polyunsaturated fatty acids on depressed mood: systematic review of published trials." Am J Clin Nutr 84(6):1308-1316 (Dec. 2006).

Atsushi Yamashita et al, J. Biochem., vol. 122, No. 1, "Acyl-transferases and Transacylases . . . ", pp. 1-16, 1997.

B. Puri et al, Archives of General Psychiatry, No. 55, "Sustained remission of positive and . . . ", pp. 188-189, 1998.

Blankenhorn D.H. et al. (1987). Beneficial effects of combined colestipol-niacin therapy on coronary atherosclerosis and coronary venous bypass grafts. JAMA 257: 3233-3240.

Brian E. Leonard, Fundamentals of Psychopharmacology, pp. 186-187, 1997.

Brown G. et al. (1990). Regression of coronary artery disease as a result of intensive lipid-lowering therapy in men with high levels of apolipoprotein B. N. Engl. J. Med. 323: 1289-1298.

Bruce J. Holub, PhD, "Fish Oils and Cardiovascular Disease", Canadian Medical Association Journal, 141(10):1063, Nov. 15, 1989.

Budavari, S., Editor, The Merck Index, 1989, Merck & Co., Inc., Rahway, N.J., entry 2417 on p. 379 and 4511 on p. 725.

Bunting et al. "Depression in Parkinson's Disease". J Neurosci Nurs. Jun. 1991; 23(3):158-164. (Abstract Only).

Canner P.L. et al. (1986). Fifteen year mortality in Coronary Drug Project patients: long-term benefit with niacin. J. Am. Coll. Cardiol. 8. 1245-1255.

Carlson L.A. & Rosenhamer G.(1988). Reduction of mortality in the Stockholm Ischaemic Heart Disease Secondary Prevention Study by combined treatment with clofibrate and nicotinic acid. Acta Med. Scand. 223: 405-418.

Clemens von Schacky, MD, Peter Angerer, MD, Wolfgang Kothny, MD, Karl Theisen, MD, and Harald Mudra, MD, "The Effect of Dietary ω-3 Fatty Acids on Cornoray Atherosclerosis: A Randomized, Double-Blind, Placebo-Controlled Trial", American College of Physicians-American Society of Internal Medicine, 130(7):554-562, 1999.

Diagnostic and Statistical Manual of Mental Disorders, 4.sup.th Ed., published by the American Psychiatric Assoc., pp. 285.

E. Mayatepek et al, The Lancet, vol. 352, "Leukotriene C4-synthesis deficiency . . . ", pp. 1514-1517, Nov. 7, 1998.

Eliz Anil, "The Impact of EPA and DHA on Blood Lipids and Lipoprotein Metabolism: Influence of apoE Genotype", Proceedings of the Nutrition Society, 66:60-68, 2007.

Frick, MH. et al (1987). Helsinki Heart Study. Primary prevention trial with gemfibrozil in middle-aged men with dyslipidaemia. Safety of treatment, changes in risk factors and incidence of coronary heart disease. N. Eng. J. Med. 317: 1237-1245.

G.J. Nelson, P.C. Schmidt, G.L. Bartolini, D.S. Kelley, and David Kyle, "The Effect of Dietary Docosahexaenoic Acid on Plasma Lipoproteins, and Tissue Fatty Acids Composition in Humans", Lipids, AOCS Press, 32(11):1137-1146, 1997.

Genest, JJ. Et al (1992). Familial lipoprotein disorders in patients with premature coronary artery disease. Circulation. 85: 2025-2033.

GISSI-Prevenzione Investigators, "Dietary Supplementation with n-3 Polyunsaturated Fatty Acids and Vitamin E after Myocardial Infarction: Results of the GISSI-Prevenzione Trial", The Lancet, 354:447-455. Aug. 7, 1999.

Glod. "Recent Advances in the Pharmacotherapy of Major Depression". Arch Psychiatr Nurs. Dec. 1996; 10(6):355-364.(Abstract Only).

Gordon, DJ. et al (1989). High density lipoprotein cholesterol and cardiovascular disease: four prospective American studies. Circulation. 79: 8-15.

Grenyer, Brin F.S., et al. "Fish Oil Supplementation in the Treatment of Major Depression: A Randomised Double-Blind Placebo-Controlled Trial" Progress in Neuro-Psychopharmacology & Biological Psychiatry 31:1393-1396 (2007).

Gro S. Rambjor, Ann I. Walen, Sheryl L. Widsor, and William S. Harris, "Eicosapentaenoic Acid is Primarily Responsible for Hypotrigylceridemic Effect of Fish Oil in Humans", Fatty Acids and Lipids from Cell Biology to Human Disease: Proceedings of the 2nd International Congress of the ISSFAL (Internaitonal Society for the Study of Fatty Acids and Lipids, AOCS Press, 31:S-45-S-49, 1996.

Hirai, A. et al. (1982). The effects of the oral administration of fish oil concentrate on the release and the metabolism of [$^{14}$C] arachidonic acid and [$^{14}$C] eicosapentaenoic acid by human platelets. Thromb. Res. 28: 285-298.

Huntington's Diease Drug Works—The DHA Dilemma http://hd-drugworks.org/index2.php?option=com_content&task=view&id=185&pop=1&pa... Printed on Aug. 22, 2008.

Ikuyoshi Watanabe et al., "Usefulness of EPA-E (eicosapentaenoic acid ethyl ester) in preventing neointimal formation after vascular injury", Kokyu to Junkan (1994), 42(7), pp. 673-677.

Jenner. "Presymptomatic Detection of Parkinson's Disease". J Neural Transm Suppl, 1993; 40:23-36. (Abstract only).

Joel A. Simon, Michael L. Hodgkins, Warren S. Browner, John M. Neuhaus, John T. Bernert, Jr., and Stephen B. Hulley, "Serum Fatty Acids and the Risk of Coronary Heart Diease", American Journal of Epidemiology, 142(5):469-476, 1995.

K.L. Black et al., "Effect of intravenous eicosapentaenoic acid on cerebral blood flow, edema, and brain prostaglandins in ischemic gerbils", Prostaglandins (1984), 28(4), pp. 545-546.

K.W. Lee and G.Y.H. Lip, "The Role of Omega-3 Fatty Acids in the Secondary Prevention of Cardiovascular Disease", Q J Med, 96:465-480, 2003.

Katsuya Yamazaki et al., "Changes in fatty acid composition in rat blood and organs after infusion of eicosapentaenoic acid ethyl ester", Biochim. Biophys. ACTA (1992), 1128(1), 35-43.

Kawano, H. et al. (2002). Changes in aspects such as the collagenous fiber density and foam cell size of atherosclerotic lesions composed of foam cells, smooth muscle cells and fibrous components in rabbits caused by all-cis 5, 8, 11, 14, 17-icosapentaenoic acid. J. Atheroscler. Thromb. 9: 170-177.

Lin, Pao-Yen, M.D., et al. "A Meta-Analytic Review of Double-Blind, Placebo-Controlled Trials of Antidepressant Efficacy of Omega-3 Fatty Acids", Psychiatry, 1056-1061 ( Jul. 2007).

M. Flint Beal, MD, Annals of Neurology, vol. 38, No. 3, "Aging, Energy, and Oxidative Stress in . . . ", pp. 357-366, Sep. 1995.

M. Sato et al., "General Pharmacological Studies on 5 8 11 14 17 Eicosapentaenoic Acid Ethyl Ester EPA-E", Folia Pharmacol JPN, (1989) 94(1), 35-48.

Malcolm Peet et al, Phospholipid Spectrum Disorder in Psychiatry pp. 1-19, 1999.

Marangell, Lauren B, M.D, et al. "A Double-Blind, Placebo-Controlled Stury of the Omega-3 Fatty Acid Docosahexaenoic Acid in the Treatment of Major Depression" Am J Psychiatry, 160(5):996-998, (May 2003).

Marian T. Childs, Irena B. King, and Robert H. Knopp, "Divergent lipoprotein Responses to Fish Oils With Various Ratios of Eicosapentaenoic Acid and Docosahexaenoic Acid", American Society for Clinical Nutrition. 52:632-9, 1990.

Martin A. Samuels, M. D. et al, Office Practice of Neurology, Chapter 122, Huntington's Disease, pp. 654-655, 1996.

Masaharu Urakaze et al., "Infusion of emulsified trieicosapentaenoylglycerol into rabbits. The effects on platelet aggregation, polymorphonuclear leukocyte adhesion, and fatty acid composition in plasma and platelet phosphollpids", Thromb. Res. (1986) 44(5), pp. 673-682.

Michael J. Finnen et al, Biochemical Society Trans., "Purification and characterisation . . . ", p. 19, 1991.

Monica Piccini et al, Genomics, vol. 47, "FACL4, A New Gene Encoding Long-Chain Acyl-CoA . . . ", pp. 350-358, 1998.

Mori, Trevor A., et al., "Docosahexaenoic Acid but Not Eicosapentaenoic Acid Lowers Ambulatory Blood Pressure and Heart Rate in Humans" Hypertension, (Aug. 1999).

N. Madhavi et al., "Effect of n-6 and n-3 fatty acids on the survival of vincristine sensitive and resistant human cervical carcinoma cells in vitro", Cancer Letters, vol. 84, No. 1, 1994, pp. 31-41.

Nemets, Boris M.D., "Addition of Omega-3 Fatty Acid to Maintenance Medication Treatment for Recurrent Unipolar Depressive Disorder" Am J Psychiatry, 159(3):477-479 (Mar. 2002).

Nina Willumsen et al, Biochimica et Biophysica Acta. vol. 1369, "On the effect of 2-deuterium- . . . ", pp. 193-203, 1998.

Obata et al. (1999) Eicosapentaenoic acid inhibits prostaglandin $D_2$ generation by inhibiting cyclo-oxygenase in cultured human mast cells.Clin. & Experimental Allergy 29: 1129-1135.

Okuda, Y. et al. (1997) Eicosapentaenoic acid enhances nitric oxide production by cultured human endothelial cells. Biochem. Biophys. Res. Commun. 232: 487-491.

Peet, Malcolm, et al. "A Dose-Ranging Study of the Effects of Ethyl-Eicosapentaenoate in Patients with Ongoing Depression Despite Apparently Adequate Treatment with Standard Drugs", Arch Gen Psychiatry, 59:913-919, (Oct. 2002).

Peter Angerer and Clemens vonSchacky, "n-3 Polyunsaturated Fatty Acids and the Cardiovascular System", Current Opinion in Lipidology, 11(1):57-63, 2000.

Philippe Dijan et al, Proc. Natl. Acad. Sci., vol. 93, "Codon repeats in genes associated . . . ", pp. 417-421, Jan. 1996.

Press Release: Amarin Corporation Says Huntington's Diease Drug Failed in Trials, http://www.fiercebiotech.com/node/6607/print (Apr. 24, 2007) Printed on Aug. 22, 2008.

Puri, B.K., et al. "Ethyl-EPA in Huntington Disease: A Double-Blind, Randomized, Placebo-Controlled Trial", Neurology 65:286-292, (2005).

Rambjor, Gro S., et al., "Eicosapentaenoic Acid is Primarily Responsible for Hypotriglyceridemic Effect of Fish Oil in Humans", Lipids 32:S-45-S-49, (1996).

Randomised trial of cholesterol lowering in 4444 patients with coronary heart disease. The Scandinavian Simvastatin Survival Study, (1994). Lancet. 344: 1383-1389.

Richard J. Woodman, Trevor A. Mori, Valerie Burke, Ian B. Puddey, Gerald F. Watts, and Lawrence J. Beilin, "Effects of Purified Eicosapentaenoic and Docosahexaenoic Acids on Glycemic Control, Blood Pressure, and Serum Lipids in Type 2 Diabetic Patients with Treated Hypertension", The American Journal of Clinical Nutrition: Official Journal of the American Society for Clinical Nutrition, Inc., 76(5):1007-1015, Nov. 1, 2002.

Rodgers, Peter J "No effect of n-3 long-chain polyunsaturated fatty acid (EPA and DHA) supplementation on depressed mood and cognitive function: a randomised controlled trial" British Journal of Nutrition, 99:421-431, (2008).

Rubins, HB et al. (1999). Gemfibrozil for the prevention of coronary heart disease in men with low levels of high-density lipoprotein cholesterol. Veterans Affairs HDL-C intervention trial study group. N. Eng. J. Med. 341: 410-418.

Rubins, HB. et al. (1995). Distribution of lipids in 8,500 men with coronary artery disease: Department of Veterans Affairs HDL Intervention Trial Study Group. Am. J. Cardiol. 75: 1196-1201.

S. L. McElroy et al., "Clozapine in the Treatment of Psychotic Mood Disorders, Schizoaffective Disorder, and Schizophrenia", Journal of Clinical Psychiatry, vol. 52, No. 10, Oct. 1991, pp. 411-414.

S. Leucht et al, Schizophrenia Research, vol. 35, "Efficacy and extrapyramidal side-effects . . . ", pp. 51-68, 1999.

S. Shah et al., "Eicosapentaenoic Acid (EPA) as an Adjunct in the Treatment of Schizophrenia", Schizophrenia Research, vol. 29, No. 1/02, Jan. 1998.

Sameline Grimsgaard, Kaare H. Bonaa, John-Bjarne Hansen, and Arne Nordoy, "Highly purified eicosapentaenoic acid and docosahexaenoic acid in humans have similar triacylglycerol-lowering effects but divergent effects on serum fatty acids" Am J Clin Nutr, 66:649-59, 1997.

Sameline Grimsgaard, Kaare H. Bonaa, John-Bjarne Hansen, and Eivind SP Myhre, "Effects of Highly Purified Eicosapentaenoic Acid and Docosahexaenoic Acid on Hemodynamics in Humans" American Society for Clinical Nutrition, 68:52-9, 1998.

Schectman, G & Hiatt, J. (1996). Drug therapy for hypercholesterolemia in patients with cardiovascular disease: factors limiting achievement of lipid goals. Am. J. Med. 100: 197-204.

Silvers, Karen M., et al. "Randomised double-blind placebo-controlled trial of fish oil in the treatment of depression," Prostagandins, Leukotrienes and Essential Fatty Acids. 72:211-218 (2005).

Stephen T. Warren, Science, vol. 271, "The Expanding World of Trinucleotide Repeats", pp. 1374-1375, Mar. 8, 1996.

Su, Kuan-Pin, et al. "Omega-3 Fatty Acids in Major Depressive Disorder A Preliminary Double-Blind, Placebo-Controlled Trial" European Neuropsychopharmacology, 13:267-271 (2003).

T.A.B. Sanders, A. Hinds and C.C. Pereira, "Influence of n-3 fatty acids on blood lipids in normal subjects" Journal of Internal Medicine. 225:99-104,1989.

Therese A. Dolecek, "Epidemiological Evidence of Relationships Between Dietary Polyunsaturated Farry Acids and Morality in the Multiple Risk Factor Intervention Trial", Society of Experimental Biology and Medicine, 200(2):177-182, 1991.

Tomohito Hamazaki, Shigeki Sawazaki, Etsuko Asaoka, Mohi Itomura, Yutaka Mizushima, Kasunaga Yazawa, Toyomi Kuwamori and Masashi Kobayashi, "Docosahexaenoic Acid-Rich Fish Oil Does Not Affect Serum Lipid Concentrations of Normolipidemic Young Adults", American Institute of Nutrition, 126(11):2784-2789, Nov. 1996.

Toshihiro Yoshimura et al, Effects of highly purified eicosapentaenoic acid on plasma beta thromboglobulin level and vascular reactivity to angiotensin II, Artery (1987) 14(5) pp. 295-303.

Vaddadi, K. S., et al. "A Randomised, Placebo-Controlled, Double-Blind Study of Treatment of Huntington's Disease with Unsaturated Fatty Acids" Clinical Neuroscience and Neuropathology, 13(1):29-33 (Jan. 2002).

Victor O. Ona et al, Nature, vol. 399, "Inhibition of caspase-1 slows disease progression . . . ", pp. 263-267, May 20, 1999.

William E. Connor, "Importance of n-3 Fatty Acids in Health and Disease", Am J Clin Nutr, 71(1(S)):171S-175S, 2000.

Wilt, VM & Gumm, JG. (1997). "Isolated" low high-density lipoprotein cholesterol. Ann. Pharmacol. 31: 89-97.

Woodman, Richard J., et al., "Effects of Purified Eicoaspentaenoic and Docosahexaenoic Acids on Glycemic Control, Blood Pressure, and Serum Lipids in Type 2 Diabetic Patients with Treated Hypertension" The American Journal of Clinical Nutrition: Official Journal of the American Society for Clinical Nutrition, Inc. 76(5):1007-1015 (Nov. 1, 2002).

Yang Cao et al, Genomics, vol. 49, "Cloning, Expression, and Chromosomal Locatlization . . . ", pp. 327-331, 1998.

Yokoyama, M. et al. (2007). Effects of eicosapentaenoic acid on major coronary events . . . Lancet 369: 1090-1098.

Hyashi, Kozo et al., "Deceases in Plasma Lipid Content and Thrombotic Activity By Ethyl Eicosapentate Purified From Fish Oils," Current Therapeutic Research, vol. 56, No. 1, 1995, pp. 24-31.

Nakamura, N. et al., "Joint effects of HMG-CoA reductase inhibitors and eicosapentaenoic acids on serum lipid profile and plasma fatty acid concentrations in patients with hyperlipidemia," International Journal of Clinical and Laboratory Research, Springer, Berlin, DE LNKD-DOI: 10.1007/S005990050057, vol. 29, No. 1, Mar. 1, 1999, pp. 22-25.

Rodriguez, Yanik, et al., "Long-chain ω6 polyunsaturated fatty acids in erythrocyte phospholipids are associated with insulin resistance in non-obese type 2 diabetics." Clinica Chimica Acta 354:195-199 (2005).

Ruiz-Narváez, E.A., et al., "Abdominal obesity and hyperglycemia mask the effect of a common APOC3 haplotype on the risk of myocardial infarction." Am J Clin Nutr 87:1932-38 (2008).

Sirtori, C.R., et al., "One-year treatment with ethyl esters of n-3 fatty acids in patients with hypertriglyceridemia and glucose intolerance—Reduced triglyceridemia, total cholesterol and increased HDL-C." Atherosclerosis 137: 419-427 (1998).

Yamamoto, K., et al., "4-Hydroxydocosahexaenoic acid, a potent Peroxisome Proliferator-Activated Receptor C agonist alleviates the symptoms of DSS-induced colitis." Biochemical and Biophysical Research Communications 367: 566-572 (2008).

International Search Report for International Application No. PCT/US2010/023638, dated May 10, 2010.

Carrero, et al., "Intake of Fish Oil, Oleic Acid, Folic Acid, and Vitamins B-6 and E for 1 Year Decreases Plasma C-Reactive Protein and Reduces Coronary Heart Disease Risk Factors in Male Patients in a Cardiac Rehabilitation Program", J. Nutr. vol. 137, pp. 384-390 (2007).

Chan, et al., "Effect of Atorvastatin and Fish Oil on Plasma High-Sensitivity C-Reactive Protein Concentrations in Individuals and Visceral Obesity", Clin. Chem., vol. 48, pp. 877-883 (2002).

Engler, et al., "Docosahexaenoic acid restores endothelial function in children with hyperlipidemia: results from the EARLY Study." International journal of Clinical Pharmacology and Therapeutics, vol. 42—No. 12/2004 (672-679).

Geppert, et al. "Microalgal docosahexaenoic acid decreases plasma triacylglycerol in normolipidaemic vegetarians: a randomized trial." British Journal of Nutrition (2006), 95, 779-786.

Hawthorne, et al., "High dose eicosapentaenoic acid ethyl ester: effects on lipids and neutrophil leukotriene production in normal volunteers." Br. J. Clin. Pharmac. (1990), 30, 187-194.

Kelley, et al., "Docosahexaenoic acid supplementation improves fasting and postprandial lip profiles in hypertriglyceridemic men." The American Journal of Clinical Nutrition, 2007; 86: 324-333.

Maki, PhD, et al., "Lipid Responses to a Dietary Docosahexaenoic Acid Supplement in Men and Women with Below Average Levels of High Density Lipoprotein Cholesterol." Journal of the American College of Nutrition, vol. 24, No. 3, 189-199 (2005).

Meyer, et al., "Dose-Dependent Effects of Docosahexaenoic Acid Supplementation on Blood Lipids in Statin-Treated Hyperlipidaemic Subjects." Lipids (2007) 42:109-115.

Nakamura, et al., "Effects of Eicosapentaenoic Acids on Remnant-like Particles, Cholesterol Concentrations and Plasma Fatty Acid Composition in Patients with Diabetes Mellitus." in vivo 12: 311-314 (1998).

Pedersen, T., et al., "Randomised trial kof cholesterol lowering in 4444 patients with coronary heart disease: the Scandinavian Simvastation Survival Study (4S)", The Lancet, No. 19, 1994, vol. 344, 8934, p. 1383-1389.

Vasudevan, "Effective Use of Combination of Lipid Therapy", Curr. Atheroscl. Rep., vol. 8, pp. 76-84 (2006).

Yamazaki, et. al., "Dissolution tests by RDC method for soft gelatin capsules containing ethyl icosapentate,", Pharm. Tech. Japan, vol. 15, No. 4, pp. 595-603 (1999). Abstract.

Gillies, et al. "Effect of a Novel Eicosapentaenoic Acid-Rich Oil on Serum Cholesterol in Man," DuPont 2010.

Guillot, et al., "Increasing intakes of the long-chain ω-3 docosahexaenoic acid: effects on platelet functions and redox status in healthy men," The FASEV Journal, vol. 23, Sep. 2009, pp. 2909-2916.

Isley, et al., "Pilot study of combined therapy with ω-3 fatty acids and niacin in atherogenic dyslipidemia," Journal of Clinical Lipidology (2007) 1, 211-217.

Nasa, et al., "Long-Term Supplementation With Eicosapentaenoic Acid Salvages Cardiomyocytes From Hypoxia/Reoxygenation-Induced Injury in Rats Fed With FishOil-Deprived Diet," Jpn. J. Pharmacol. 77, 137-146 (1998).

Nestel, et al., "The n-3 fatty acids eicosapentaenoic acid and docosahexaenoic acid increase systemic arterial compliance in humans," Am J Clin Nutr 2002; 76:326-330.

Parks, Omacor FDA (CDER) Medical Review, Oct. 2004.

Sanders, et al., "Influence of an algal triacylglycerol containing docosahexaenoic acid (22:6n-3) and docosapentaenoic acid (22:5n-

6) on cardiovascular risk factors in healthy men and women," British Journal of Nutrition (2006), 95, 525-531.

Tatarczyk, et al., "Analysis of long-chain ω-3 fatty acid content in fish-oil supplements," Wien Klin Wochenschr (2007) 119/13-14: 417-422.

Terano, et al., "Effect of Oral Administration of Highly Purified Eicosapentaenoic Acid on Platelet Function, Blood Vicosity and Red Cell Deformability in Healthy Human Subjects," Atherosclerosis, 46 (1983) 321-331.

Zuijdgeest-van Leeuwen, et al., "N-3 Fatty Acids Administered as Triacylglycerols or as Ethyl Esters Have Different Effects on Serum Lipid Concentrations in Healthy Subjects," N-3 Fatty Acids, Lipid Metabolism and Cancer, Feb. 2000, pp. 89-100.

Hamazaki T., et al., "Reduction in microalbuminuria in diabetics by eicosapentaenoic acid ethyl ester" Lipids. 25 (9):541-545 (Sep. 1990).

Nishikawa M., et al., "Effects of eicosapentaenoic acid (EPA) on prostacyclin production in diabetics: GC/MS analysis of PG12 and PG13 levels" Methods Find Exp Clin Pharmacol. 19(6):429-433 (Jul.-Aug. 1997).

Nozaki S., et al. "Effects of purified eicosapentaenoic acid ethyl ester on plasma lipoproteins in primary hypercholesterolemia" Int J Vitam Nutr Res. 62(3):256-260 (1992).

Shinozaki K., et al., "The long-term effect of eicosapentaenoic acid on serum levels of lipoprotein (a) and lipids in patients with vascular disease" J Atheroscler Thromb. 2(2):107-9 (1996).

Tsuruta K., et al., "Effect of purified eicosapentaenoate ethyl ester on fibrinolytic capacity in patients with stable coronary artery disease and lower extremity ischaemia "Coron Artery Dis. 7(11):837-42 (Nov. 1996).

Westerveld H.T., et al., "Effects of low-dose EPA-E on glycemic control, lipid profile, lipoprotein(a), platelet aggregation, viscosity, and platelet and vessel wall interaction in NIDDM" Diabetes Care 16(5):683-8 (May 1993).

Yamamoto H., et al., "Improvement of coronary vasomotion with eicosapentaenoic acid does not inhibit acteylcholine-induced coronary vasospasm in patients with variant angina" Jpn Circ J. 59(9):608-16 (Sep. 1995).

Chemical Book, Eicosapentaenoic acid ethyl ester, copyright 2010, printed Jun. 16, 2011 from www.chemicalbook.com.

Hamazaki, et al., "Effects of Orally Administered Ethyl Ester of Eicosapentaenoic Acid (EPA; C20:5, omega-3) on PGI2-Like Substance Production by Rat Aorta," Prostaglandins, Apr. 1982, vol. 23 No. 4, pp. 557-567.

Press Release from Mochida Pharmaceutical Co., Ltd.: Conclusion of Distributorship Agreement Concerning Switch-OTC Drug for Hyperlipidemia Treatment, Epadel, published Apr. 30, 2009.

Tamura, et al., "Study of the Clinical Usefulness of Ethyl Icosapentate (MND-21) in Long-Term Treatment of Hyperlipaemic Patients," J Clin Thera & Medicines 1991; 7:1817-1834.

\* cited by examiner

Figure 1. The synthesis of eicosapentaenoic acid from alpha-linolenic acid

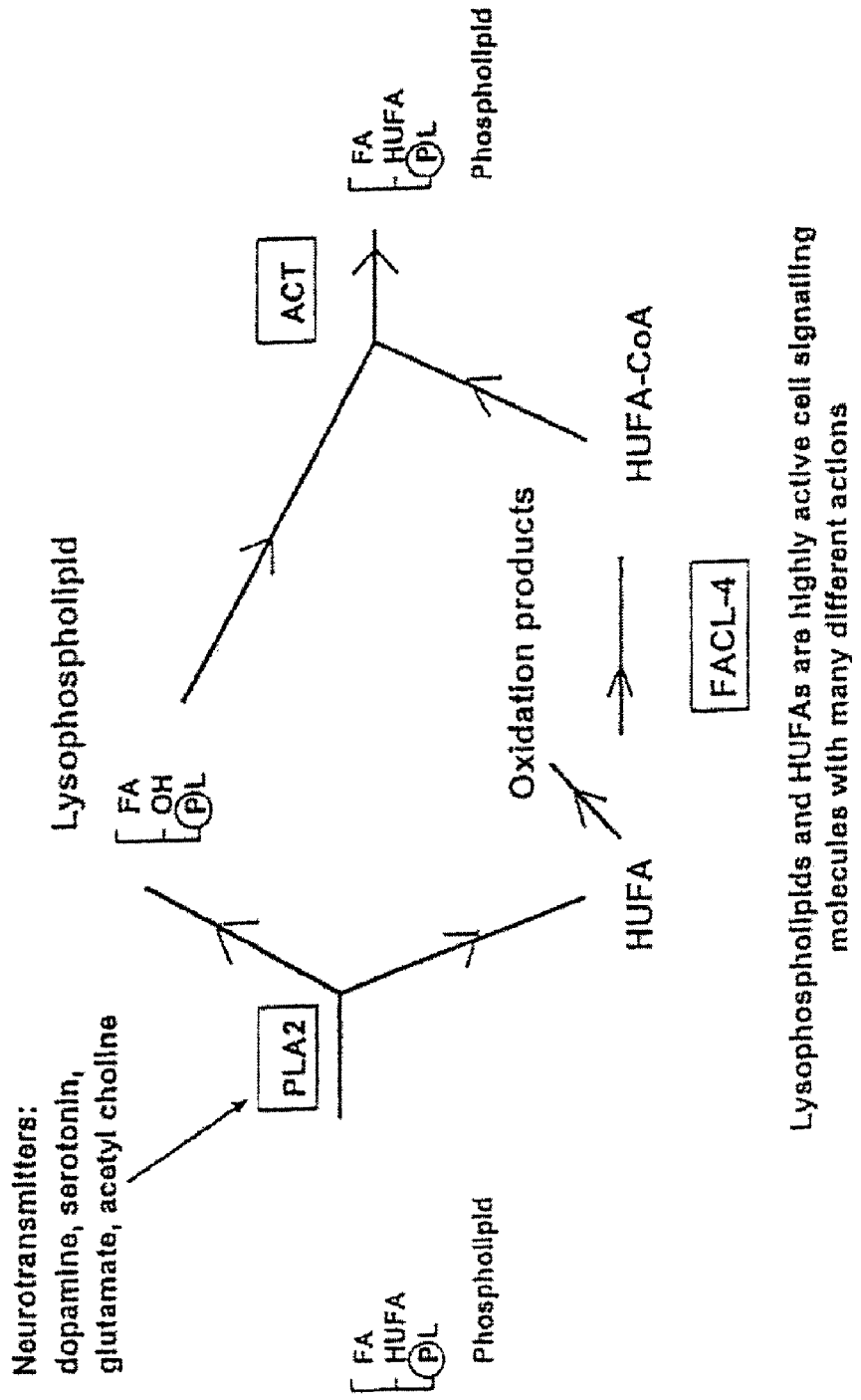

HIGHLY PURIFIED ETHYL EPA AND OTHER EPA DERIVATIVES

Even though many new drugs have been discovered over the past twenty years, psychiatric disorders are still relatively poorly treated. With most psychiatric illnesses, drug treatments do not treat all patients successfully. This is true of schizophrenia, schizoaffective and schizotypal disorders, bipolar disorder (manic-depression), unipolar depression, dementias, panic attacks, anxiety, sleep disorders, attention, hyperactivity and conduct disorders, autism, personality disorders, and all other psychiatric conditions. For example, in depression, standard drugs achieve a 50% reduction in standard depression scores in about two thirds of patients: the others do not respond. In schizophrenia, the average improvements are only of the order of 20-30% (S Leucht et al, Schizophrenia Research 1999; 35:51-68) although individual patients may do much better than this.

The same is true of neurological disorders like Alzheimer's disease and other dementias, Parkinson's disease, multiple sclerosis, stroke, epilepsy and Huntington's disease. Again, many patients fail to respond to existing treatments, or respond only to a limited degree. In none of these conditions do existing drugs reliably produce a complete remission of symptoms. There is therefore a great need for new treatments, particularly ones which have novel mechanisms of action.

In PCT filing WO98/16216 attention was drawn to the value of a particular fatty acid, eicosapentaenoic acid (EPA), and its derivatives, in the treatment of schizophrenia, depression and dementias. EPA is a highly unsaturated fatty acid which can be derived from the dietary essential fatty acid, α-linolenic acid by a series of three reactions (FIG. 1). EPA is a fatty acid containing 20 carbon atoms and 5 double bonds, all in the cis-configuration. The double bonds are located at the 5, 8, 11, 14 and 17 positions and the full chemical name is therefore all cis (or all z) 5, 8, 11, 14, 17-eicosapentaenoic acid (or sometimes icosapentaenoic acid).

Figure 2:
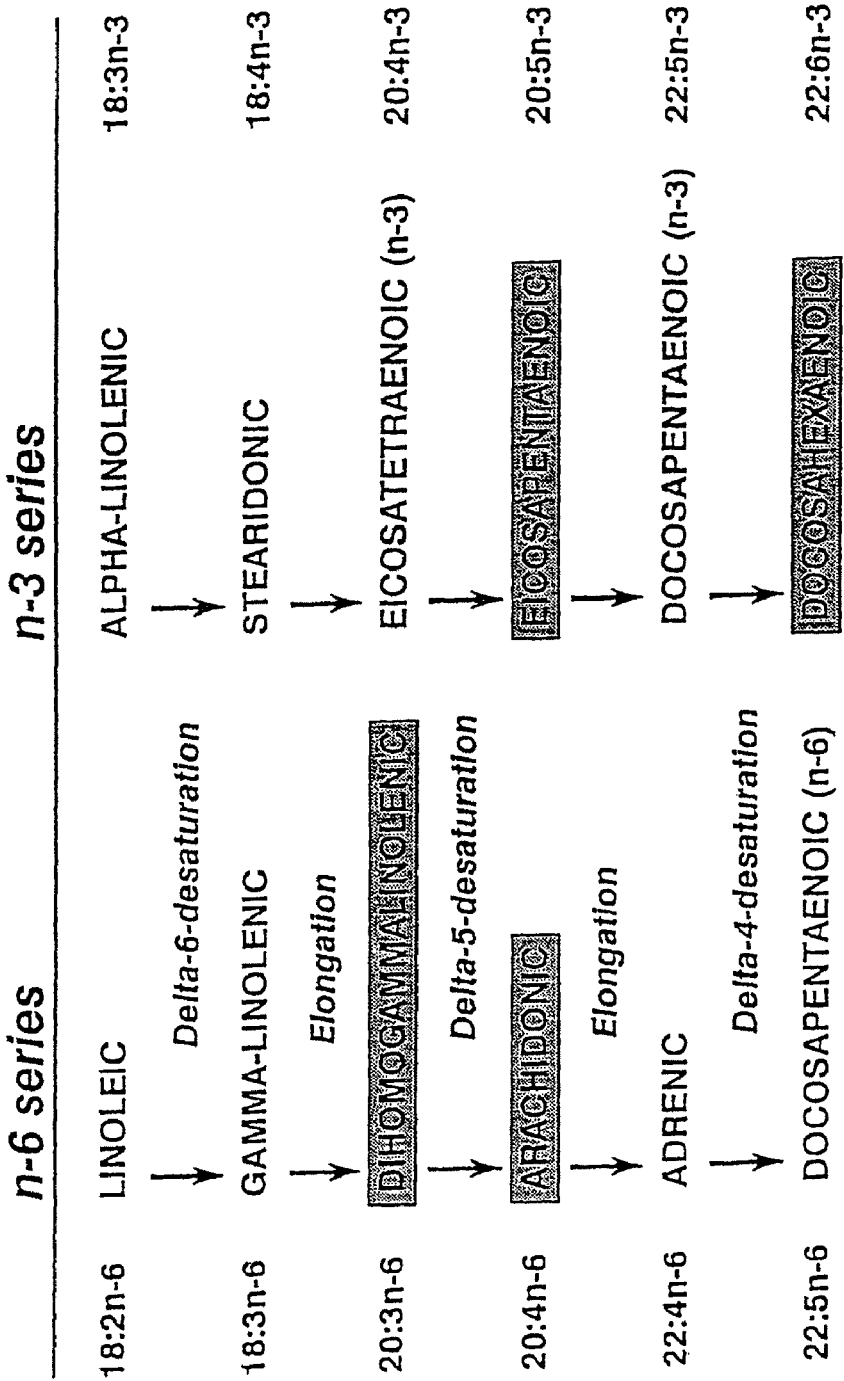

The abbreviation which is always used is EPA. EPA is one of the highly unsaturated fatty acids, the main types of which are shown in FIG. 2. The reactions which convert alpha-linolenic acid to EPA are slow in humans and only a very small proportion of dietary α-linolenic acid is converted to EPA. EPA is also found in marine micro-organisms and, via the food chain, makes up between 3% and 30% of natural marine oils derived from oily fish and marine mammals. EPA is found linked to many different chemical structures. It can be found in the form of phospholipids, tri, di- and monoglycerides, amides, esters of many different types, salts and other compounds. In each case the EPA moiety can normally be split from the complex molecule to give the free acid form which can then be linked again to other complex molecules.

As described in PCT filing WO 98/16216 it was unexpectedly found that an oil enriched in EPA was of value in treating schizophrenia, while an oil enriched in the closely related fatty acid, docosahexaenoic acid (DHA), was not. This was surprising because DHA is found in large amounts in human brain whereas EPA is found only in trace quantities. It was therefore anticipated that DHA would be effective but EPA would not. In fact the opposite was found. WO 98/16216 disclosed the use of EPA and its derivatives for the treatment of psychiatric disorders.

The present invention provides a pharmaceutical preparation comprising EPA in an appropriately assimilable form where of all the fatty acids present in the preparation at least 90%, and preferably at least 95%, is in the form of EPA and where less than 5%, and preferably less than 3%, is in the form of docosahexaenoic acid. Such preparations are for the treatment of any disorder except peripheral vascular disease and hyper-triglyceridaemia.

Preferably, among the other fatty acids present there are less than 5%, and preferably less than 3%, of each of AA or DPA-n-3, individually. The same preferably applies for any other fatty acids which might compete with the EPA.

It is preferred that the aggregate DHA, AA and/or DPA-n-3 content is less than 10%, of the total fatty acids present, and preferably less than 5%.

The EPA may be in the form of ethyl-EPA, lithium EPA, mono-, di- or triglyceride EPA or any other ester or salt of EPA, or the free acid form of EPA. The EPA may also be in the form of a 2-substituted derivative or other derivative which slows down its rate of oxidation but does not otherwise change its biological action on psychiatric or brain disorders to any substantial degree (N. Willumsen et al., Biochimica Biophysica Acta, 1998, 1369: 193-203). Such pharmaceutical preparations may be used for the treatment of a psychiatric or central nervous system disorder, including: schizophrenia, schizoaffective disorder or a schizotypal disorder; depression or manic-depression (bipolar disorder); anxiety or panic disorder or social phobia, or a sleep disorder or an attention deficit, conduct, hyperactivity or personality disorder; autism; Alzheimer's disease, vascular dementia or another dementia, including multi-infarct dementia, Lewy body disease and diseases attributable to prion disorders; Parkinson's disease, or other motor system disorder; multiple sclerosis; stroke; epilepsy; and Huntington's disease or any other neuro-degenerative disorder.

The present invention further provides formulations for use in psychiatric and neurological disorders in which a drug which acts primarily on neurotransmitter metabolism or receptors is prepared for co-administration with a pharmaceutical preparation according to the first aspect of the invention, as well as pharmaceutical formulations comprising a preparation according to the first aspect of the invention together with a drug which acts primarily on neurotransmitter metabolism or receptors. The conventional drug may administered in conventional dosage, and the EPA formulations according to the first aspect of the invention administered to the patient separately. The conventional drug may be combined with the EPA preparations of the first aspect of the invention in a combination formulation, or the two may be provided in separate individual formulations but in a combination pack.

The EPA-containing preparations of the present invention may be administered with any drug known to have an effect on the treatment of psychiatric or central nervous system disorders to improve the efficacy of the drug or reduce its side effects.

Suitable drugs for co-administration with the EPA preparations of the first aspect of the invention are clozapine; and any one of the class of typical or atypical neuroleptics, including chlorpromazine, haloperidol, risperidone, olanzapine, sertindole, ziprasidone, zotepine or amisulpiride. Others are mentioned below.

The present invention still further provides a method of treating or preventing the side effects of a drug used in treating psychiatric or neurological disorders by administration of the drug and a pharmaceutical preparation according to the first aspect of the present invention.

It is important in treatment of psychiatric disorders to use pure or nearly pure EPA and EPA derivatives. It is a surprising conclusion that DHA and related fatty acids may not only be ineffective but may actually reduce the efficacy of EPA and its derivatives.

Phospholipids are the main components of nerve cell membranes. In nerve cells the middle carbon atom of phospholipids, known as Sn2, is usually attached to a highly unsaturated fatty acid (HUFA) such as DHA, arachidonic acid (AA), and sometimes EPA. HUFAs are fatty acids containing 18-26 carbon atoms and three or more double bonds. When nerve cells are activated, for example by dopamine or serotonin, the activity of a group of enzymes collectively known as phospholipase $A_2$ ($PLA_2$) is frequently increased. $PLA_2$ releases the HUFA from the Sn2 position, giving a free molecule of HUFA and a molecule of what is known as a lysophospholipid (LyPL) (a phospholipid without a fatty acid attached to the Sn2 position) (FIG. 3). Both of these molecules can be highly active cell signalling agents themselves, and can change cell function in a number of different ways. In addition, the HUFA can be converted to prostaglandins, leukotrienes, hydroxy acids and a whole range of short-lived molecules which regulate neuronal function. For example, one of these molecules derived from arachidonic acid, leukotriene C4, seems to be absolutely required for normal nerve cell growth and development (E Mayatepek and B Flock, Leukotriene C4-synthesis deficiency: a new inborn error of metabolism linked to a fatal developmental syndrome Lancet 1998; 352: 1514-7).

If cell function is to be normal, it is important that this activation should be temporary and should be terminated by removing the free HUFA and the LyPL. Otherwise membrane damage may result because the LyPL can be destructive. Furthermore the free HUFAs are easily oxidised to highly active free radicals which can do great damage. There is an emerging consensus that such membrane damage is a fundamental pathological basis for many neurodegenerative disorders, including Alzheimer's disease and other dementias, Parkinson's disease, stroke, Huntington's disease, all types of ischaemic damage, and multiple sclerosis. A range of initiating causative factors may all cause damage by the same common route. Phospholipid breakdown to LyPLs and free HUFAs may also be important in epilepsy.

The signal transduction processes involving HUFAs and LyPLs are terminated in most cases by a two sequence reaction. First, the HUFA is linked to coenzyme A by a group of enzymes known as fatty acid coenzyme A ligases (FACLs). These enzymes are also known as acyl-CoA synthetases. The HUFA-coenzyme A derivative is then linked to the LyPL by a group of enzymes known as acyl CoA: lysophospholipid acyltransferases (ACLATs) which liberate coenzyme A in the process (A Yamashita et al, Acyltransferases and transacylases involved in fatty acid remodelling of phospholipids and metabolism of bioactive lipids in mammalian cells. J Biochem 122: 1-16, 1997). This sequence thus removes from the nerve cell the HUFAs and the LyPLs and brings to an end the events associated with signal transduction, so preparing the neuron for the next stimulus (FIG. 3).

There is now a substantial amount of evidence which demonstrates that in the three major psychotic mental illnesses there is increased activity of one or more of the phospholipase group of enzymes and particularly in one or more of the $PLA_2$ group. These three illnesses are schizophrenia, bipolar disorder and major depression: the three disorders are often found together in the same families, and often have overlapping ranges of symptoms. It has long been thought that at least part of their biochemical basis is common to all three disorders and it is possible that the $PLA_2$ abnormality constitutes that common factor. In schizophrenia, there are increasing circulating levels of $PLA_2$ in the blood. In bipolar disorder, lithium, which is the main established treatment, has been shown to inhibit the activity of $PLA_2$. In major depression, there is depletion of HUFAs of the n-3 series from membranes, coupled with activation of inflammatory responses which occurs with enhanced activity of $PLA_2$. Each of those illnesses, however, involves more than one biochemical abnormality: while a $PLA_2$ or related phospholipase abnormality may be common to all three, the other abnormalities are probably specific to each disease.

In schizophrenia, it has recently been discovered that there is a second abnormality in the fatty acid cycle. This is a deficit in function of FACL-4, the enzyme which links HUFAs to coenzyme A in human brain (Y Cao et al, Cloning, expression and chromosomal localization of human long-chain fatty acid-CoA ligase 4 (FACL4) Genomics 1998; 49: 327-330). It is known that there is a defect in the incorporation of HUFAs into phospholipids in schizophrenia but the precise enzyme has not been known. However, FACL-4 is found in brain, is specific for HUFAs, and when absent produces both brain abnormalities and also minor physical abnormalities such as a high arched palate which are typical of patients with schizophrenia (M Piccini et al, FACL-4, a new gene encoding long-chain acyl-CoA synthetase 4, is deleted in a family with Alport Syndrome, elliptocytosis and mental retardation. Genomics 1998; 47:350-358). It is the combined presence of both the enzyme abnormalities which produces the disease.

The second or other abnormalities in bipolar disorder and in major depression are not yet known. Another phospholipase, PLC, which acts at the Sn3 position to liberate inositol phosphates and diacylglycerol may be involved in bipolar disorder. Both of these molecules, like LyPL and HUFAs, are involved in cell signalling: overactivation of both PLC and $PLA_2$ is likely to be related to bipolar disorder.

In the neurodegenerative conditions there appears to be an uncontrolled activation of membrane degrading enzymes like phospholipases, coupled with increased formation of free radicals associated with the oxidation of HUFAs and the membrane damage produced by LyPL. This type of phenomenon, with membrane damage associated with excess phospholipase activity, has been well described by many investigators in Alzheimer's disease and other dementias, in multiple sclerosis, in stroke and other brain disorders caused by ischaemia or injury, in Parkinson's disease, in epilepsy and in Huntington's disease. In attention deficit disorder, also known as hyperactivity, there are deficits in the blood of the highly unsaturated fatty acids which can be acted upon by phospholipases.

In all of these situations, therefore, there is some evidence of increased phospholipase activity and signal transduction activity which may not be terminated in a normal way. Thus the phospholipases, FACLs and acyl-transferases present new targets for drug action. Our observation that EPA-enriched materials are beneficial in psychiatric disorders may therefore be explained in several ways:

EPA is known to inhibit phospholipase $A_2$ (M J Finnen & C R Lovell, Biochem Soc Transactions, 1991; 19:915) and so will help to down regulate the initial activation process. Interestingly, in this assay system, the related fatty acid docosahexaenoic acid (DHA) had no effect.

EPA has an unusually high affinity for the human brain enzyme FACL-4 (Y Cao et al, 1998 see above). Usually with enzymes which act on HUFAs, the activities with HUFAs like EPA, DHA and AA are similar, or very frequently, DHA and AA are more active than EPA. With FACL-4, however, activity for AA was more than twice as great as for DHA, whereas that for EPA was 50% greater than for AA (Y Cao et al, 1998). This means that EPA will more readily than other HUFAs enter the cycle, form an EPA-COA derivative, link to LyPL and so terminate the activity of free LyPL. Thus EPA will, more effectively than other HUFAs, stop the activation once it has started.

Because EPA will compete with AA for incorporation into the Sn2 position of phospholipids, EPA will also reduce the amount of AA incorporated into that position. This is likely to be particularly important in depression, where AA levels are relatively or absolutely abnormally high. EPA itself is a HUFA which can be converted to desirable compounds like prostaglandin $I_3$ ($PGI_3$) and prostaglandin $E_3$ ($PGE_3$) which have a range of anti-inflammatory and antithrombotic actions which may be particularly useful in neurodegenerative disorders and in depression. The compounds derived from EPA appear to be less potentially harmful than the equivalent compounds derived from AA. Replacement of AA by EPA is therefore likely to be of particular value in all the neurodegenerative disorders described above, where at least part of the damage is attributable to overactive phospholipases which release AA which can then be converted to pro-inflammatory compounds.

The purification of EPA is difficult and complex. Because its five double bonds must all be in the right positions in the carbon chain and must all be in the cis configuration, EPA is difficult to synthesize. In nature EPA is almost always found mixed with other fatty acids in the forms of triglycerides and phospholipids. The principles of purification of EPA are well known to those skilled in the art and include low temperature crystallisation, urea fractionation, lithium crystallisation, fractional distillation, high pressure liquid chromatography, supercritical carbon dioxide chromatography and various other forms of chromatography using silica gels and other column packings. The application of these known techniques has been difficult to apply in practice on a large scale and only recently has pure EPA (more than 90% pure and preferably more than 95% pure) become available for testing in psychiatric and CNS disorders. In one version of the purification process, natural fish oil triglycerides rich in EPA are saponified and the fatty acids converted to the ethyl ester form. A preparation enriched in ethyl EPA is then prepared by molecular distillation with collection of the appropriate fraction. This fraction is then converted to a preparation containing over 80% of ethyl EPA by urea precipitation. The final preparation of more than 96% pure ethyl EPA is then achieved by either silica gel chromatography or high pressure liquid chromatography.

Conventionally, most studies on the uses of EPA and related fatty acids have used materials partially enriched in EPA but also containing substantial amounts of other fatty acids, especially docosahexaenoic acid (DHA) which is found alongside EPA in most natural oils. The fatty acids have usually been in the triglyceride or ethyl ester forms, and occasionally in the free acid and phospholipid forms. Docosapentaenoic acid (DPA n-3) is also a common component of such materials. The new understanding of possible mechanisms of action of EPA which we have developed has, however, led to the realisation that the purer is the EPA the better is likely to be the activity. This is not just a question of dose, although that is indeed a valuable aspect of the application of pure EPA. From the point of view of a patient, particularly a mentally disturbed patient, it is obviously better to give, say, 1 g of EPA as a 95% pure preparation than, say, 5 g of a 19% pure preparation providing the same total amount of EPA. The patient is much more likely to comply with the lower volumes required with the highly purified compound.

More importantly, other fatty acids such as AA, DPAn-3, and DHA, which are relatively similar in structure to EPA, but do not share the same spectrum of biological activity, compete with EPA for binding to the active sites of all the relevant enzymes. Thus these other fatty acids will compete with EPA for occupation of these active sites and reduce its activity. The purer the preparation of EPA the more likely is it to occupy the relevant active binding sites, and the more likely is it to be able to have desirable biological effects.

Our attention was unexpectedly drawn to the importance of highly purified EPA by our experience with a patient, a depressed women aged 35 years. She had had a long history of depression with Hamilton Depression Rating Scale scores ranging from 15 to 25. Trials of several different antidepressants, including traditional tricyclic compounds and newer selective serotonin reuptake inhibitors had failed to have an impact. Because of evidence of the importance of EPA in depression she was given a three months trial of 4 g/day of an EPA enriched fish oil containing 25% of EPA, together with 8% of DHA and 10% of other highly unsaturated fatty acids. At the start of this trial she had a Hamilton score in the 20-22 range and at the end a Hamilton score in the 16-18 range, a small but not very important improvement.

She continued the EPA-rich oil for a further two months without any further change. A 96% pure preparation of ethyl-EPA with less than 3% DHA then became available to me and it was suggested that the woman should switch from taking 4 g/day of the 25% EPA preparation to 1 g/day of the 96% preparation. We expected that this would be more convenient but did not expect any clinical improvement because the EPA daily dose remained unchanged. However, surprisingly, after about 3-4 weeks she began to experience a major improvement with Hamilton scores falling below 6 for the first time for several years. As a result of this, and of thinking about the evidence relating to the binding of EPA to FACL-4 and presumably to other proteins, we came to the conclusion that it was important for clinical efficacy to administer EPA in a highly purified form for maximum clinical effectiveness. Surprisingly, the same daily dose of EPA in a purified form seems considerably more effective than that dose when mixed with other fatty acids which may compete with EPA for binding to the relevant sites of action.

This initial experience has now been confirmed by many other case reports in a range of psychiatric disorders. Some examples of the observations made include the following:

Schizophrenia: A patient with a ten-year history had been well controlled by taking 16×0.5 g capsules a day of fish oil containing 24% of EPA and 8% of DHA. This provided around 1.9 g/day of EPA and 0.6 g/day of DHA. He was not taking other antipsychotic drugs. However, he did not like taking the high doses of fish oils and tried to reduce the dose. However, when he did this the symptoms returned and it was concluded that he had to take around 2 g/day of EPA to remain well. When the purified ethyl-EPA became available, he was switched to 4×0.5 g capsules, also providing around 2 g/day. This controlled his symptoms very well. He therefore dropped the dose to 1 g/day. Unlike the previous situation with the mixed fish oil providing 1.9 g/day of EPA and 0.6 g/day of DHA, reducing the ethyl-EPA dose to 1 g/day did not lead to a recurrence of symptoms. 1 g/day in pure form therefore appeared as effective and possibly more effective than 1.9 g per day of EPA when mixed with DHA and other fatty acids.

Bipolar disorder: Bipolar disorder is a condition in which either a depressive or a manic state is episodic, or in which depressive or manic states alternate. The standard treatments are lithium or valproate derivatives, or the antipsychotic neuroleptic drugs which are particularly used to control the manic states. Standard antidepressants are sometimes used but they have to be applied with caution because there is a risk that they may precipitate a manic state. Very high doses (9-10 g/day) of mixed EPA and DHA have been reported to be helpful in managing bipolar patients, improving depression and reducing the risk of relapse into either a depressive or a manic episode (A Stoll et al, Omega-3 fatty acids in bipolar disorder. Archives of General Psychiatry, 1999; 56: 407-412). Prior to the availability of the pure ethyl-EPA, five patients with bipolar disorder, whose condition was only partially controlled by lithium with intermittent neuroleptics to control the manic episodes, were given 10-20 g/day of a fish oil containing 18% of EPA and 12% of DHA. This provided 1.8 B 3.6 g of EPA and 1.2 B 2.4 g of DHA per day. On this treatment the patients were less depressed, and less prone to mood swings, as indicated by following their clinical course for over a year. They were, however, far from completely normal. When the pure ethyl-EPA became available, they were switched from the fish oil to the pure EPA at a dose of 2 g/day in the form of four 0.5 g soft gelatin capsules. In each case their clinical condition improved considerably. Their depressions became substantially better and they showed less tendency to mood swing. In particular they all noted an improvement in something which is difficult to measure by conventional psychiatric rating scales. This is a sense of inner tension or dysphoria, a state which is associated with the illness, but which may be exaggerated or changed by antipsychotic drugs to a state of confused tension, sometimes described as a sense of the brain being replaced by cotton wool, and a difficulty of thinking clearly in a straight line. Remarkably, the patients reported that this sense of dysphoria, tension and "cotton-wool thinking" was greatly reduced or disappeared altogether. They had not noticed this effect which being treated with the higher dose of EPA in the form of the EPA/DHA mix in fish oil. Thus again the purified EPA had a greater and qualitatively different effect from the mixed EPA and DHA, supporting the idea that DHA actually reduces the therapeutic effect of EPA, and that highly purified EPA is therapeutically more effective.

Attention deficit hyperactivity disorder (ADHD): ADHD and closely related conditions like attention deficit disorder and conduct disorders are commonly found in children. Occasionally they may be successfully treated by behaviour modification and other psychological techniques or by careful attention to diet. However, in most cases, paradoxical treatment with one of the stimulant drugs related in their action to amphetamine is required. Methylphenidate and dextroamphetamine are the commonest used. A seven year old boy with serious ADHD since infancy was driving his parents to distraction. Psychological measures and diet had completely failed, and his condition was only partially controlled by methylphenidate. The parents were concerned about the long term consequences of stimulant drugs. The boy was therefore tried on two capsules of pure ethyl-EPA per day. There was little change for the first two weeks but then a substantial improvement in behaviour developed. The boy became less tense and irritable, less hyperactive, more open to reasoned discussion and enormously less disruptive both at home and school. Even when his methylphenidate was stopped, his behaviour remained improved.

Dementia: A 75 year old woman developed dementia, probably of Alzheimer type but possibly with multi-infarct contributions because of associated cardiovascular disease. As often occurs she also became withdrawn and depressed but, unfortunately, this state was interrupted by irrational and violent outbursts, usually directed at members of her family, but also sometimes against complete strangers. She was tried on two cholinergic drugs: although these produced a small improvement in her cognitive state they did nothing for her depression, irritability and anger. She was tried on a dose of 4×0.5 g capsules of pure ethyl-EPA, two given in the morning and two in the evening. Within four weeks she had experienced a remarkable improvement, becoming more cheerful and friendly and showed a substantially reduced irritability. Her family also thought her cognition had improved but this is difficult to be certain of because of her improved mood.

Panic and anxiety disorders are very common. They are associated with panic attacks which may come out of the blue with no precipitating factors at all, or may be associated with mildly stressful situations which in normal people would evoke no such reactions. The characteristics of panic attacks are a feeling of severe anxiety, difficulty in breathing, sweating, a feeling of abdominal discomfort known as "butterflies in the stomach" and a feeling of legs collapsing. Very frequently associated with all these psychological symptoms, there is also a tachycardia, which is associated with a subjective sensation of cardiac palpitations. Insomnia is common, and patients frequently wake up spontaneously in the middle of the night with palpitations and panic. Patients are also frequently depressed. Common treatments include anti-anxiety drugs such as benzodiazepines, beta-blockers to control the palpitations and anti-depressants.

We have now treated several patients who have panic and anxiety disorders with purified ethyl-EPA with excellent effect. Three case histories follow. A 29 year old woman was disabled as a result of frequent and uncontrollable panic attacks and palpitations. Treatments with benzodiazepines, beta-blockers and antidepressants had proved only partially effective in controlling her symptoms. She was then given a dose of 2 g per day of ethyl EPA as four 500 mg capsules. Her symptoms dramatically improved and over a period of three months her panic attacks and palpitations were almost absent, with only two relatively mild attacks. This treatment was much more effective than any previous treatment she had received. A 56 year old woman had suffered from mild anxiety and panic attacks for most of her life but these had become much worse over the previous few years in association with various problems with her children. Anxiolytics and antidepressants had only modest effects and her palpitations were uncontrolled even by relatively high doses of beta-blockers. Again she was treated with ethyl-EPA over a period of four months. Her anxiety and panic attacks became much less severe, and even when they occurred were free of palpitations which had previously worried her a great deal. The third patient was a 55 year old housewife who had been through two divorces and was now in a long-term relationship. She had several panic attacks every week, sometimes in the middle of the night, and always accompanied by strong palpitations which were very worrying for her. These panic attacks were accompanied by depression. She was very reluctant to go out for fear of having an attack and this seriously disrupted her life. Again, antidepressants, beta-blockers and anxiolytics had had only limited beneficial effects. She was also treated with ethyl-EPA and over a period of four months experienced a dramatic reduction in her panic attacks and palpitations. Sometimes, she felt that an attack of palpitations might be coming on but it rarely materialised. As a result, she felt increasing confidence and was able to resume a much more normal life. These observations demonstrate that purified ethyl-EPA is effective in the management of panic disorder.

Another use for ethyl-EPA is as an adjunct to the management of severe depression when using electroconvulsive therapy (ECT). ECT is used most other treatments have failed to be helpful. It involves the administration of shocks under anaesthesia and, although effective, is used with reluctance by both patients and doctors because of fears that it may damage the brain and cause memory loss. Anything from five to twenty or even more shocks may be given during a course of treatment. It would be highly desirable to be able to limit the numbers of shocks required to achieve a beneficial effect and in a small number of patients we have found that this is indeed the case.

These observations indicate that pure ethyl-EPA is of value in a wide range of psychiatric and neurological disorders, reflecting the common involvement of membrane and phospholipid abnormalities in these conditions.

But E-EPA is not only useful as a therapy by itself. E-EPA can be co-administered with standard drugs used in various psychiatric and neurological conditions and can substantially enhance the response to standard therapy, and also reduce many of the side effects of standard therapy. The present invention provides combination therapy involving the co-administration of E-EPA with standard drugs, either involving the same formulation or the same packaging.

Our attention was drawn to this possibility by a striking case history. A middle aged male patient with a long history of schizophrenia had failed to respond to therapy with "typical" neuroleptics. "Typical" neuroleptics are drugs with a strong blocking action on dopamine $D_2$ receptors (B Leonard, Fundamentals of Psychopharmacology, $2^{nd}$ edition, Wiley, New York, 1997). This mechanism is thought to be responsible for their rapid effects on the so-called "positive" symptoms of schizophrenia (such as hallucinations, delusions and thought disorder). These drugs, however, have little effects on the so-called "negative" symptoms of schizophrenia such as anhedonia, lack of affect, and emotional and social withdrawal. The $D_2$ blocking action is also responsible for many of the adverse effects of these drugs, which include extrapyramidal movement disorders, excess prolactin secretion, and tardive dyskinesias. Examples of widely used drugs in this class include chlorpromazine, thioridazine, haloperidol, pimozide, flupenthixol and sulpiride.

In spite of treatment with full doses of several of these drugs the patient failed to respond. He was therefore put on the first of the so-called "atypical" neuroleptics, clozapine. These atypical drugs have a much lower affinity for $D_2$ receptors, and often have a wide range of other receptor actions. These may include blockade of one or more of the other dopamine receptors such as $D_1$, $D_3$ or $D_4$, and also usually including blockade of one or more classes of serotonin receptors. They do not cause much prolactin secretion and rarely cause extrapyramidal movement disorders. They may also have actions at other receptors, including histamine, glutamate and acetyl choline receptors.

Drugs in this class include clozapine, olanzapine, quetiapine, risperidone, ziprasidone, sertindole and perhaps zotepine and amisulpiride. There are many drugs of this type in early development, all characterised by a lower affinity for $D_2$ receptors than the "typical" neuroleptics.

The patient was treated with clozapine, eventually reaching a maximum dose of 900 mg/day. This produced some improvement but the patient remained severely ill. He was tense, withdrawn and suspicious and exhibited bizarre behaviour. For example, he refused to allow any sound when he turned on the television set because of his paranoia about people speaking to him. This was naturally irritating to anyone attempting to watch television with him. The patient was given trials of olanzapine, quetiapine and risperidone with no substantial benefit. Clinically he appeared to do best on clozapine and so was maintained for many months on 900 mg/day. The main side effect of clozapine which bothered him was the hypersalivation.

E-EPA in a dose of 2 g/day was then administered in addition to clozapine. Although EPA is an effective treatment for schizophrenia, its onset of action is slow and substantial benefits are not normally seen until 4-8 weeks after starting treatment (B Puri et al, Sustained remission of positive and negative symptoms of schizophrenia following treatment with eicosapentaenoic acid, Archives of General Psychiatry 55:188-189, 1998). However, in this clozapine-treated patient who had been so seriously ill for many years, the effects began to be apparent within days and were dramatic within two weeks. They were noted both by the patient himself and by family and friends. In particular, instead of being depressed he became cheerful, instead of being tense he became relaxed, instead of being withdrawn and refusing to speak, he become outgoing and chatty. For his family and friends, one of the first and most striking effects was that he allowed the television to be on with a normal sound level. The psychiatrist in charge of the patient noted "I cannot remember ever seeing such a dramatic improvement in a schizophrenic illness in less than 2 weeks". A particularly important aspect of this case is that the clozapine-induced hypersalivation was considerably reduced.

In this patient, clozapine and other neuroleptics, both typical and atypical, clearly had very limited beneficial effects. On the other hand E-EPA had a surprisingly large and unexpectedly rapid effect which is not normally seen if E-EPA is administered alone. This suggests a strong beneficial interaction between clozapine and E-EPA and suggests that clozapine and E-EPA should be administered together in at least some patients.

There are good reasons why E-EPA should have additive and even synergistic effects in association with conventional psychotropic drugs, not only for schizophrenia but also for all other psychiatric and neurological disorders. This is because most drugs used for the management of psychiatric and neurological disorders act on neurotransmitter metabolism or on neurotransmitter receptors, modulating the synthesis, inactivation, reuptake or responses to neurotransmitters such as noradrenaline, serotonin, dopamine, glutamate, acetyl choline, and gamma-aminobutyric acid (GABA). However, many phenomena in nerve cells occur after a receptor has been occupied by a neurotransmitter or blocking agent. Receptor occupation leads to many changes in cellular function which go under the general name of "signal transduction" or "cell signalling" and which include changes in G proteins, in calcium movements, in sodium and potassium movements, in metabolism of phospholipids and eicosanoids, in cyclic nucleotide changes, and in gene regulation. These are only some examples of the processes which take place under the general heading of signal transduction. The specific example of activation of the $PLA_2$ cycle which may follow activation of dopamine, serotonin, acetyl choline or glutamate receptors is shown in FIG. 3.

There is increasing evidence that some of the abnormalities which cause psychiatric and neurological disorders are not at the neurotransmitter or receptor level but are at the post-receptor signal transduction level. Much of this evidence in relation to psychiatric disorders has been summarised in a recently published book (Phospholipid Spectrum Disorder in Psychiatry, ed. M Peet, I Glen & D F Horrobin, Marius Press, Carnforth, UK, 1999). If this is so, then drugs like most of these currently in use, which act at the neurotransmitter or receptor level, will only have limited efficacy. This is true of drugs for many types of psychiatric and neurological disorders, most of which have their primary actions at the neurotransmitter or receptor level. Diseases currently treated by drugs affecting neurotransmitter metabolism or neurotransmitter receptors include schizophrenia, depression, bipolar disorder, attention deficit, conduct and related disorders, Parkinson's disease, dementias, anxiety, panic and social phobic disorders, and premenstrual syndrome. The current drugs would be expected to have additive or synergistic effects with drugs which act at the post-receptor signal transduction level, since then the drug combination would be acting at two different levels in the neuron.

The main effect of E-EPA is to modulate post-receptor phospholipid-related signal transduction. Indirectly these actions then modulate other processes or enzymes such as protein kinases, calcium movements, cyclic nucleotide metabolism or gene expression. There are therefore strong and potentially valuable interactions between EPA and any of these other classes of drug.

This case history of the single patient has unexpectedly drawn our attention to a general principle, namely the idea that E-EPA or indeed any other form of biologically active EPA may be usefully co-administered with any psychotropic or neurological drug which primarily acts on neurotransmitter metabolism or neurotransmitter receptors.

The drugs which may usefully be co-administered with EPA include typical and atypical antischizophrenic drugs, antidepressants of all classes, drugs used in control of anxiety or panic, drugs used to regulate sleep, and drugs used in the management of Parkinson's disease or dementia. All these drugs act primarily at the level of neurotransmitters or their receptors.

The general principle that E-EPA can potentiate the effects of standard drug treatments can be illustrated by further case histories. A 50 year old man who suffered from severe depression had been tried on several antidepressants without effect. Eventually he was treated with a selective serotonin reuptake inhibitor (SSRI) called citalopram which, surprisingly, relieved some of his depression even though other SSRIs had failed. This produced an improvement which was sustained for several months although during this time he continued to be moderately depressed. In addition to citalopram he was then given 1 g/day of ethyl-EPA. After four weeks, for the first time in several years, he experienced a lightening of mood and regained much of the interest in life which he thought he had lost forever. Another case was a young woman of 21 who dropped out of college with a schizophrenic breakdown. She experienced auditory hallucinations which kept telling her that one of her professors was out to destroy her college career, she became totally distrustful about her close student friends, and she produced a bizarre series of assignment essays which illustrated severe thought disorder. She was treated with 10 mg/day olanzapine which stopped the hallucinations, reduced the paranoia and thought disorder but, she claimed, made her dysphoric and "fuzzy" and unable to think clearly.

It also made her very sleepy, and gave her a large appetite causing her to put on weight. She was given 2 g/day ethyl-EPA and after about 4 weeks claimed to be thinking more clearly, and to have a reduced appetite allowing her to lose weight. After a year she was able to return to college where again she consistently performed at the A and B grade level.

A 40 year old man had become ill with schizophrenia at the age of 25. He had florid hallucinations and paranoia, but also withdrew himself from most of his friendships and lived alone. He was tried on various drugs, some of which produced side effects which he did not like. Eventually a dose of the typical neuroleptic, haloperidol, was found which stopped most of the hallucinations and kept his paranoia within reasonable bounds, but seemed to make him even more withdrawn. He lived alone, ceased to communicate with most of his friends, and went around to town alone and muttering to himself. His psychiatrist heard about ethyl-EPA and decided to try it in addition to the standard drug.

After eight weeks on treatment with 4 g/day his outlook was transformed. His residual hallucinations disappeared and he became emotionally much warmer and more friendly. He was even persuaded to go on holiday with his family where he enjoyed himself and made new friends. The EPA therefore reversed the extreme withdrawal which appeared to have been exaggerated by haloperidol.

The typical neuroleptics in some patients produce a distressing condition called tardive dyskinesia. This is due in part to irreversible changes in the brain since the condition often does not remit if drug treatment is stopped. The patient experiences uncontrollable twitching and other movements. These can affect any part of the body but commonly affect the face where they are particularly distressing. Facial twitches and movements, including protrusions and uncontrollable movements of the tongue occur. Several patients we have treated with EPA have experienced substantial relief from tardive dyskinesia. Movements have become substantially less and in some patients have disappeared completely.

Clozapine is regarded as a particularly effective drug by many psychiatrists but it has a range of severe side effects. From the patient's point of view one of the most troublesome is hypersalivation. This may not sound very serious but the constant flow of large volumes of saliva is in fact very distressing for the patient and for those who are associated with the patient. The mechanism of the hypersalivation is unknown. Completely unexpectedly, in three clozapine-treated patients for whom hypersalivation was a major problem, treatment with ethyl-EPA not only caused a substantial improvement in psychiatric state, but also dramatically reduced the salivation to normal levels to the great relief of the patients and their careers.

Obesity is another common side effect of antipsychotropic drugs. In this respect some of the newer drugs like olanzapine frequently seem to be even worse offenders than the typical neuroleptics. A young woman who had had a schizophrenic breakdown in her early-twenties had been treated with typical neuroleptics for about 10 years and then for the past two years with olanzapine. She preferred the olanzapine but it still left her withdrawn and unable to communicate normally with friends or family. To her distress it caused her to put on over 10 kg in weight. Her doctor decided to test ethyl-EPA in addition to olanzapine. Over the next six months her withdrawn state gradually improved and she began to perform again as a musician which she had not done for several years. Equally important for her self-esteem she lost most of the weight which she had gained when she first started on olanzapine.

These case histories clearly demonstrate the following:
1. Pure ethyl-EPA has strong therapeutic effects in its own right on schizophrenia, bipolar disorder, depression, attention deficit disorder and dementia. Like other drugs with antipsychotic actions it is likely to have some beneficial effects in most psychiatric disorders and also in neurological disorders associated with membrane damage. These include the various types of dementia (including Alzheimer's disease, multi-infarct vascular dementia and Lewy body disease), multiple sclerosis, Parkinson's disease and Huntington's chorea.

2. Pure ethyl-EPA enhances the beneficial effects of a wide range of psychiatric and neurological drugs. This makes a great deal of sense since it is increasingly apparent that many abnormalities in psychiatry and neurology lie beyond the neurotransmitter receptor in the signal transduction systems of neurons and other cells. EPA acts on these signal transduction systems, providing a rational explanation for the positive interactions between EPA and other drugs.
3. Completely unexpected was the ability of EPA to reduce the adverse effects of psychiatric and neurological drugs. The mechanism is unknown but it appears to be a relatively general phenomenon as it has been noted with drug-induced obesity, movement disorders, sedation, dysphoria and salivation.

Although the case reports of the effects of ethyl-EPA are convincing and in some cases dramatic, unequivocal proof of its efficacy must come from randomised, placebo-controlled trials. We therefore set up a randomised, placebo-controlled study of EPA in 34 patients who had schizophrenia according to the criteria set out in the American Psychiatric Association's Diagnostic and Statistical Manual of Mental Disorders ($4^{th}$ edition, DSM-IV). All of these patients were being treated with clozapine drugs but all remained seriously ill, with schizophrenic symptoms. Like many schizophrenics, some of the patients were also depressed. All were assessed at baseline and after 12 weeks using the Positive and Negative Symptom Scale for Schizophrenia (PANSS) and the Montgomery-Asberg Depression Rating Scale (MADRS).

After giving informed consent, all the patients were randomised on a double blind basis to one of three groups: placebo, or 1 g or 2 g of ethyl-EPA per day in the form of 0.5 g capsules. Placebo and EPA capsules were indistinguishable from one another in appearance.

The percentage changes from baseline in the four groups are shown in the table. All the patients improved to some degree so all the changes are percentage improvements

| rating scale | Placebo | 1 g EPA | 2 g EPA |
| --- | --- | --- | --- |
| Total PANSS | 5.2% | 18.8% | 17.1% |
| positive PANSS | 9.5% | 20.0% | 25.0% |
| negative PANSS | 11.1% | 22.7% | 22.7% |
| MADRS | 13.3% | 35.7% | 35.7% |

As can be seen, on all the rating scales the EPA groups did substantially better than the placebo group. E-EPA (ethyl-EPA) was effective in reducing symptoms of schizophrenia, symptoms of depression and side effects of existing drugs. The simultaneous effect on depression, as indicated by the MADRS scale, and schizophrenia, as indicated by the PANSS scale, is particularly important. These results therefore confirm the individual patient reports and demonstrate unequivocally that E-EPA has a strong therapeutic effect.

Of particular note is the fact that there were no reported side effects attributable to the E-EPA and no differences at all between placebo and active treatment in the side effects which were reported. This means effectively that, in dramatic contrast to almost all other drugs used in psychiatry or neurology, EPA has no important side effects at all.

Huntington's disease is in many respects the most devastating of all diseases which affect the brain. It is a dominantly inherited genetic disorder which usually becomes manifest between the ages of 30 to 50 and leads to death after a course which usually lasts about 15-25 years. Half of the children of patients will also develop the disease (W J Koroshetz, pp. 654-661 in A Office Practice of Neurology, ed MA Samuels & S Feske, Churchill Livingstone, N.Y., 1996).

The affected gene is for a protein called huntingtin located on chromosome 4p16.3. The gene contains a polymorphic trinucleotide CAG repeating area. In normal individuals the number of CAG repeats is usually less than 35, whereas in Huntington's disease the number of repeats is higher than this. The longer the number of repeats, the earlier the disease is likely to develop. The repeats result in overexpression of huntingtin which forms aggregates in the affected neurons. The aggregates may be associated with membranes and with the cytoskeleton and cause malfunction and eventually death of the neurons concerned. There can be damage to almost any part of the brain but it is particularly evidence in the basal ganglia structures, the caudate and the putamen.

Several other neurological diseases are now known to be associated with excessive numbers of trinucleotide repeats in other genes. It is believed that similar mechanisms of protein accumulation and neuronal damage may be involved (ST Warren, The expanding world of trinucleotide repeats, Science 1996; 271:1374-1375: P Djion et al, Coden repeats in genes associated with human diseases, Proceedings of the National Academy of Sciences of the USA 1996; 93:417-421). In addition to Huntington's disease, the illnesses known to be caused in this way include fragile X syndrome, Friedreich's ataxia, spinal and bulbar muscular atrophy, spinocerebellar ataxia type I, dentato-rubral-pallidoluysian atrophy, Haw River syndrome, Machado-Joseph disease, and myotonic dystrophy.

Huntington's disease can manifest an extraordinary wide range of symptoms and signs (W J Koroshetz, 1996) and can exhibit features of schizophrenia, depression, anxiety, irritability, loss of emotional control, epilepsy, Parkinson's disease and dementia. It has been suggested that the fundamental end mechanism in a wide range of neurological diseases, including Huntington's disease, amyotrophic lateral sclerosis, Parkinson's disease, Alzheimer's disease and other dementias, and cerebellar degeneration is oxidative damage to membranes and to proteins (M F Beal, Aging, energy and oxidative stress in neurodegenerative diseases, Annals of Neurology 1995; 38: 357-366). It is postulated that in these diseases, normal or abnormal proteins aggregate and damage internal and external membranes. The differences between the diseases relate to the nature of the proteins and to the site of the neurons most affected, but the overall processes are similar.

In a typical patient with Huntington's disease, the illness beings with mild motor incoordination, forgetfulness, slowness to perform actions and emotional liability with irritability. The incoordination then progresses to obvious neurological damage with sudden jerking movements, and repeated uncontrollable writhing and restlessness, a pattern going under the general name of chorea. There is often marked weight loss, possibly in part related to the "exercise" produced by the uncontrollable movements. Eventually the patient ceases to be able to walk, becomes demented with severe memory loss, and requires 24 hour nursing care. Death is often caused by pneumonia due to aspiration of food or liquid into the lungs as a result of inability to swallow normally.

No known treatments are of any substantial value. The abnormal movements and the psychosis may respond partially to standard anti-schizophrenic drugs, while antidepressants, tranquillizers, and anti-epileptic drugs may help to relieve some symptoms transiently. Nothing stops the inexorable downhill course.

Because early Huntington's disease may present with schizophrenia-like features, a randomised trial of 96% pure ethyl-EPA was set up in seven severely disabled patients in the final stages of Huntington's disease. All required 24 hour nursing care, had severe movement disorders, were irritable and were partially demented. They were randomised on a double blind basis to receive 2 g/day ethyl-EPA or 2 g/day placebo for 6 months. During the 6 month period, four patients showed progressive deterioration while three patients reversed the course of the disease and showed improvement with reduced abnormal movements, reduced emotional liability and irritability and improved memory and cognitive function. When the code was broken all four patients who deteriorated were found to be on placebo, while all three patients who improved were found to be taking ethyl-EPA. In four of the patients, two on ethyl-EPA and two on placebo, the brain degeneration was assessed at the beginning and end of the study by magnetic resonance imaging (MRI). MRI allows an accurate assessment of the size of the lateral ventricles, the fluid-filled spaces within the cerebral hemispheres. As Huntington's disease progresses, the lateral ventricles enlarge indicating loss of brain tissue. In the two patients on placebo over 6 months the ventricles enlarged as expected. In the two patients on ethyl-EPA, the MRI showed a reduction in lateral ventricle size indicating an actual reversal of brain tissue loss.

These dramatic results in patients in the end stage of a previously untreatable disease caused by abnormal protein accumulation demonstrate the value of ethyl-EPA in neurodegenerative disorders. Such disorders are all associated with membrane damage, oxidative stress and activation of phospholipases. EPA is able to repair membranes, to inhibit phospholipases and to enhance antioxidant defenses. The Huntington's results therefore support the use of pure ethyl-EPA in the neurological disorders associated with trinucleotide repeats, and those associated with oxidative membrane damage which may sometimes be due to abnormal protein accumulation, including Alzheimer's disease and other dementias, Lewy body dementia, Parkinson's disease, epilepsies, multiple sclerosis, stroke and head injury and post-stroke and post-injury syndromes, and diseases of animals and humans due to prion accumulation such as kuru, bovine spongiform encephalopathy, Creutzfeldt-Jacob disease and scrapie.

Very recently it has been shown that Huntington's disease is associated with activation of an enzyme called caspase I or interleukin converting enzyme (ICE). This enzyme is involved in a wide range of neurodegenerative brain diseases. It generates interleukin-1-beta which activates a wide range of pro-inflammatory, cell-damaging actions (V O Ona et al, Inhibition of caspase-I slows disease progression in a mouse model of Huntington's disease. Nature 1999; 399: 263-267). One possible additional mechanism of ethyl-EPA action is therefore inhibition of caspase-I.

The present invention has identified ethyl-EPA as being highly effective. However, it is likely that any form of highly purified EPA which is able to raise EPA levels in the blood is of value in psychiatric disorders. These EPA compounds will all be of value in the treatment of psychiatric and neurological disorders when prepared in pure form. It will always be important to keep to the absolute minimum the presence of related fatty acids, which might interfere with the EPA. The compounds which are known, but which have not previously been prepared or proposed in such pure forms for use in psychiatric and CNS disorders are:
1. Ethyl-EPA which is widely used in Japan for the treatment of cardiovascular disorders.
2. Lithium-EPA which was previously disclosed in U.S. Pat. No. 5,252,333 but which was not then distinguished from any other lithium HUFA derivative as being of particular value in psychiatric disorders. The value of this derivative lies in the fact that lithium itself is a treatment of choice in bipolar disorder and is also known to have therapeutic effects in schizophrenia, schizoaffective disorder and depression. Recently it has been demonstrated that inhibition of PLA2 and of the PLC inositol phosphate cycle are important actions of lithium. Since EPA has related actions, the lithium derivative of EPA will be of particular value.
3. Triglycerides, monoglycerides or diglycerides in which more than 90% and preferably more than 95% of the fatty acids present in the molecule consist of EPA.
4. Other esters and compounds capable of delivering fatty acids to the body in which more than 90% and preferably more than 95% of the fatty acids present are in the form of EPA.

In each of the above cases there should be less than 5% and preferably less than 36 of DHA, DPA or AA or other competing fatty acids individually. In aggregate there should be less than 10% and preferably less than 5% of these competing fatty acids.

These compounds, in 90% and preferably 95% or even purer forms, may all be administered orally via delivery systems known to those skilled in the art, including soft and hard gelatin capsules; microcapsules in powder, tableted or capsule form; tablets for the solid compound, lithium-EPA; or emulsions made with appropriate natural or synthetic emulsifying agents, including phospholipids or galactolipids. The compounds may also be administered parenterally, either directly, or formulated in various oils or in emulsions or dispersions, using either intravenous, intraperitoneal, intramuscular or sub-cutaneous routes. Topical applications using patch technology or vaginal or rectal forms of application are within the range of the invention.

The EPA compounds may advantageously in some patients be coadministered with other drugs used in psychiatry and neurology. Such drugs may include drugs of the typical neuroleptic class such as chlorpromazine, haloperidol, thioxanthene, sulpiride, droperidol, perphenazine, loxapine, thioridazine, fluphenazine, pericyazine, methotrimeprazine or pimozide among others: clozapine: drugs of the atypical neuroleptic class including olanzapine, risperidone, sertindole, ziprasidone, quetiapine, zotepine and amisulpiride; drugs which have antidepressant actions including tricyclic and related antidepressants, noradrenaline reuptake inhibitors, serotonin reuptake inhibitors, monoamine oxidase inhibitors and drugs with atypical antidepressant actions: drugs for sleep disorders, anxiety disorders, panic disorders, social phobias, conduct disorders, personality disorders and attentional deficit hyperactivity disorder; drugs for any form of dementia, including Alzheimer's disease, vascular and multi-infarct dementias, Lewy body disease and other dementias; drugs for any form of neurological disease including Parkinson's disease, multiple sclerosis, Huntington's disease and other neurodegenerative disorders.

In each of the above cases, the EPA compound and the other drug may be administered separately, each in their own formulation. They may be packaged separately or be present in the same overall package. Alternatively, using techniques well known to those skilled in the art, the EPA and other drug may be formulated together, so that a daily dose of EPA of 0.1 g to 10 g per day, and preferably of 0.5 g to 5 g per day, is provided with the normal daily dose of the other drug.

When supplied alone, the useful daily dose of EPA may be in the range of 0.05 g to 50 g/day, preferably 0.1 g to 10 g/day and very preferably 0.5 g to 5 g/day.

It has previously been suggested that omega-3 fatty acids like EPA may be valuable in the treatment of inflammatory disorders of the joints, respiratory system, gastro-intestinal system, kidneys, skins, reproductive system and all other organs. However, the importance of the purity of EPA has not previously been recognised. The invention will therefore be valuable in these disorders also and the present invention also provides pharmaceutical compositions for the treatment of such inflammatory disorders.

FIG. 1 shows the pathway by which eicosapentaenoic acid (EPA) is synthesised within the human body from alpha-linolenic acid. FIG. 2 shows the other essential fatty acids which are related in structure to EPA. FIG. 3 shows the role of phospholipase $A_2$ in signal transduction in nerve cells. Various neurotransmitters, including dopamine, activate $PLA_2$ which leads to the formation of a lysophospholipid and a HUFA, both of which activate the cell. The activation is terminated by a fatty acid coenzyme A ligase (FACL), particularly FACL-4, which links coenzyme A to the HUFA, and then by an acyl coenzyme A transferase (ACT) which links the HUFA-coenzyme A to a lysophospholipid. In the process coenzyme A is liberated, a stable phospholipid molecule is reformed and the activation process is terminated.

Other EPA derivatives which could be used are the 2-substituted derivatives of EPA described by N Willumsen, I Vaagenes, H Holmsen and R K Berge (Biochim Biophys Acta 1369: 193-203, 1998). These have the advantage of having a longer duration of action because they are less readily oxidised.

EXAMPLE

Formulations

In each of the following examples the product is at least 90% and preferably 95% or more pure. This is very important as other fatty acids will compete with the EPA for the binding sites and reduce its efficacy. In particular, fatty acids such as DHA, AA, DPA-n-3 will, individually, be present in concentrations of less than 5% and preferably less than 3%. The total aggregate of such competing compounds must be less than 10% and preferably less than 5%. This degree of purity is also valuable in minimising the volume of material which must be consumed each day, a major factor in helping compliance in psychiatric patients where lack of compliance is a serious problem.

1. Capsules made of hard or soft gelatin which contain 250 mg, 500 mg, or 1000 mg of ethyl-EPA, triglyceride EPA or other appropriate form of EPA.
2. Tablets containing 250 mg, 500 mg or 1000 mg lithium-EPA or hard gelatin capsules containing similar amounts.
3. Emulsions, solutions or dispersions in which the lithium-EPA, ethyl-EPA, triglyceride EPA or other appropriate form of EPA are prepared in a palatable liquid form for oral administration.
4. Suppositories or pessaries into which 100 mg to 5 g of one of the EPA compounds are formulated.
5. Intravenous solutions or emulsions containing from 10 mg to 500 mg/ml of one of the EPA compounds.
5-10. As examples 1-5, but using 2-substituted derivatives of EPA.
11-20. As in 1-10 but in which the EPA compound is formulated with the usual dose of any other drug used for the treatment of psychiatric or neurological disorders.
21-30. As in 1-10 but in which the EPA compound is formulated with clozapine.

The invention claimed is:

1. A pharmaceutical composition comprising one or more fatty acids, at least 95% of which are in the form of ethyl-eicosapentaenoic acid, wherein the composition contains no docosahexaenoic acid and the composition is present in a capsule.

2. The composition of claim 1 wherein the composition contains less than 3% of any fatty acid other than eicosapentaenoic acid.

3. The composition of claim 2 wherein the capsule is a gelatin capsule.

4. The composition of any one of claim 1, 2, or 3 wherein the ethyl-eicosapentaenoic acid is present in the composition in an amount of 250 mg to 1000 mg.

5. A pharmaceutical composition comprising 250 mg to 1000 mg of fatty acids at least 95% of which are in the form of ethyl eicosapentaenoic acid, wherein the composition contains no docosahexaenoic acid, and the composition is present in a capsule.

6. A pharmaceutical composition comprising 250 mg to 1000 mg of fatty acids at least 95% of which are in the form of ethyl-eicosapentaenoic acid, wherein the composition contains (a) less than 5% in aggregate of arachidonic acid and n-3 docosapentaenoic acid, and (b) no docosahexaenoic acid; and wherein the composition is present in a capsule.

7. The pharmaceutical composition of claim 5 wherein the composition contains arachidonic acid in an amount less than 3%, by weight, of said fatty acids.

8. The pharmaceutical composition of claim 6 wherein the composition contains docosapentaenoic acid in an amount less than 3%, by weight, of said fatty acids.

9. The pharmaceutical composition of claim 6 wherein the composition contains arachidonic acid and docosapentaenoic acid in an aggregate amount of less than 3%, by weight, of said fatty acids.

10. The pharmaceutical composition of claim 6 wherein the capsule comprises about 1000 mg of said composition.

* * * * *